United States Patent
Benes et al.

(10) Patent No.: US 9,072,797 B2
(45) Date of Patent: Jul. 7, 2015

(54) IMMUNOCONJUGATE FOR HUMAN CD66 FOR THE TREATMENT OF MULTIPLE MYELOMA AND OTHER HAEMATOLOGICAL MALIGNANCIES

(75) Inventors: Ivan Benes, Forch (CH); Klaus Bosslet, Berlin (DE); Kim Orchard, Hampshire (GB)

(73) Assignee: THERAPHARM GMBH, Zug (CH)

( * ) Notice: Subject to any disclaimer, the term of this patent is extended or adjusted under 35 U.S.C. 154(b) by 1645 days.

(21) Appl. No.: 12/097,508

(22) PCT Filed: Nov. 30, 2006

(86) PCT No.: PCT/EP2006/011533
§ 371 (c)(1),
(2), (4) Date: Jul. 7, 2009

(87) PCT Pub. No.: WO2007/062855
PCT Pub. Date: Jun. 7, 2007

(65) Prior Publication Data
US 2010/0183505 A1   Jul. 22, 2010

Related U.S. Application Data

(60) Provisional application No. 60/740,647, filed on Nov. 30, 2005.

(51) Int. Cl.
*A61K 51/10* (2006.01)
*A61K 47/48* (2006.01)
*C07K 16/28* (2006.01)

(52) U.S. Cl.
CPC .................................. *A61K 51/1069* (2013.01)

(58) Field of Classification Search
CPC ........... A61K 51/1069; A61K 51/1045; A61K 47/48076; C07K 16/2803
See application file for complete search history.

(56) References Cited

U.S. PATENT DOCUMENTS 6,241,961 B1   6/2001   Benes et al.

FOREIGN PATENT DOCUMENTS

WO   WO 02/12347      2/2002
WO   WO 2004/029093   4/2004

OTHER PUBLICATIONS

Yu et al, Investigative Ophthalmology & Visual Science 49(2): 522-527, Feb. 2008.*
Witte et al, Cancer and Metastasis Reviews 17: 155-161, 1998.*
Stancovski et al, Proceedings of the National Academy of Science USA 88: 8691-8695, 1991.*
Riemer et al, Mol. Immunol. 42: 1121-1124, 2005.*
Tol et al, N Engl J Med. 360(6):563-72, Feb. 5, 2009.*
Cooper et al., Bioconjugate Chem 23: 1029-1039, 2012.*
Borchardt et al., J Nuclear Medicine 39(3): 476-484, Mar. 1998.*
Bunjes et al., "Clinical Observations, Interventions, and Therapeutic Trials: Rhenium 188-labeled anti-CD66 (a, b, c, e) monoclonal antibody to intensify the conditioning regimen prior to stem cell transplantation for patients with high-risk acute myeloid leukemia or myelodysplastic syndrome: results of a phase I-II study," 2001, Blood, 98, 565-572.
Harsdorf et al., "Allogeneic stem cell transplantation for multiple myeloma: Effect of T cell depletion and donor lymphocyte infusions (DLI)," 2000, Onkologie, vol. 23, No. Sonderheft 7, pp. 123.
Jurcic JG, "Antibody therapy of acute myelogenous leukemia," 2000, Cancer Biother Radiopharm, 15, 319-326.
Kotzerke et al., "Basic Science Investigations: Radioimmunotherapy for the Intensification of Conditioning Before Stem Cell Transplantation: Differences in Dosimetry and Biokinetics of $^{188}$Re- and $^{99m}$Tc-Labeled Anti-NCA-95 MAbs," 2000, Journal of Nuclear Medicine, 41, 3, 531-537.
Matthews et al., "Clinical Observations, Interventions, and Therapeutic Trials: Phase I Study of $^{131}$I-Anti-CD45 Antibody Plus Cyclophosphamide and Total Body Irradiation for Advanced Acute Leukemia and Myelodysplastic Syndrome," 1999, Blood, 94, 1237-1247.
Ringhoffer et al., "188Re or 90Y-labelled anti-CD66 antibody as part of a dose-reduced conditioning regimen for patients with acute leukaemia or myelodysplastic syndrome over the age of 55: results of a phase I-II study," 2005, British Journal of Haematology, 130, 604-613.
Terpos et al., "Current treatment options for myeloma." 2005, Expert Opin Pharmacother, 6(7): 1127-1142.
Karban et al., "Expression of CD66 in non-Hodgkin Lymphomas and Multiple Myeloma," European Journal of Haematology 85 (496-501) , 2010.
Satoh et al., "Expression of CD66a in Multiple Myeloma," Journal of Clinical Laboratory Analysis, 16:79-85 (2002).

* cited by examiner

*Primary Examiner* — Phuong Huynh
(74) *Attorney, Agent, or Firm* — Kilpatrick Townsend & Stockton LLP

(57) ABSTRACT

The present invention relates to the use of radioimmunoconjugates for the treatment of haematological malignancies, particularly multiple myeloma.

11 Claims, 21 Drawing Sheets

FIG. 1  *White blood cell count pre and post Y-90 labelled anti-CD66.*
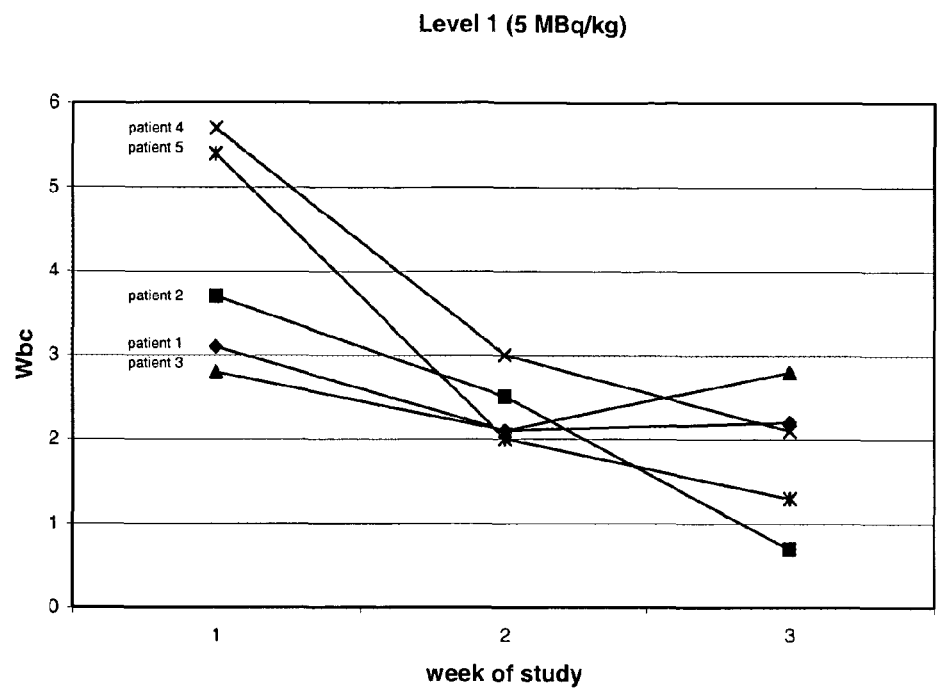
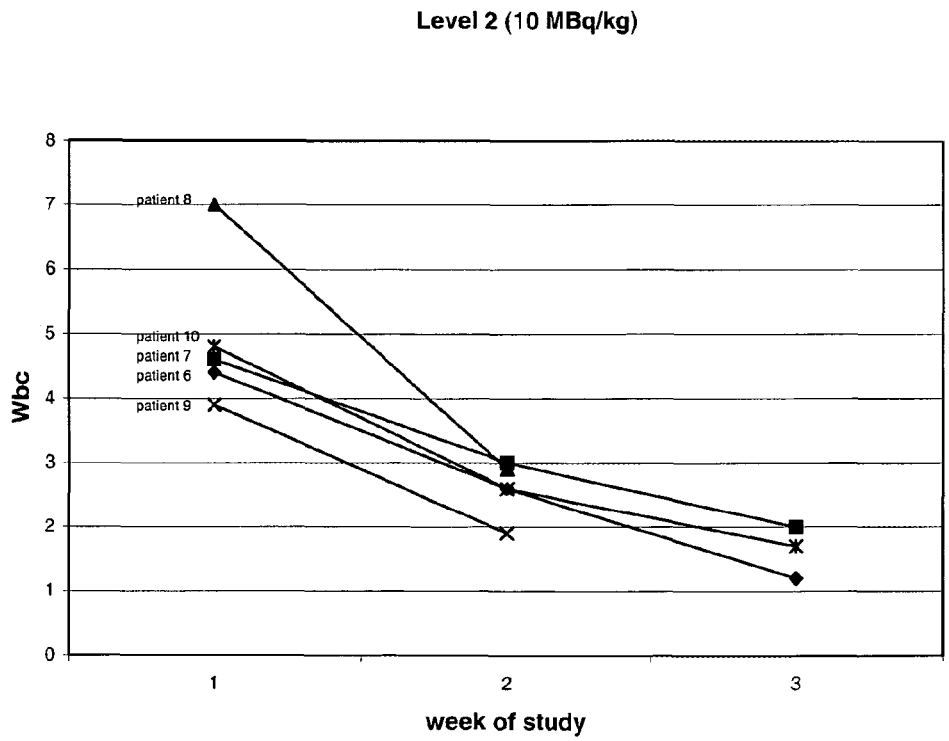

FIG. 2  *Neutrophil count pre and post Y-90 labelled anti-CD66 Mab*
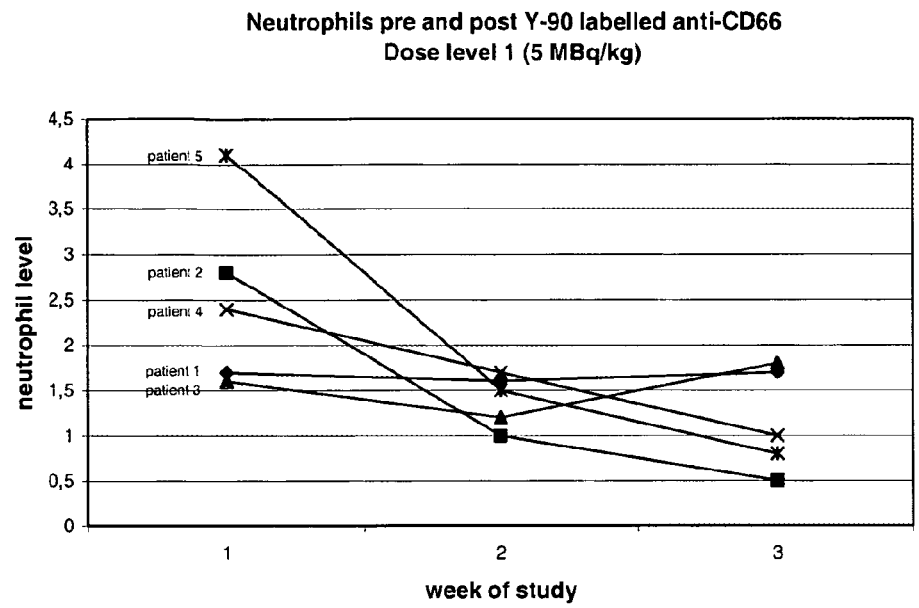
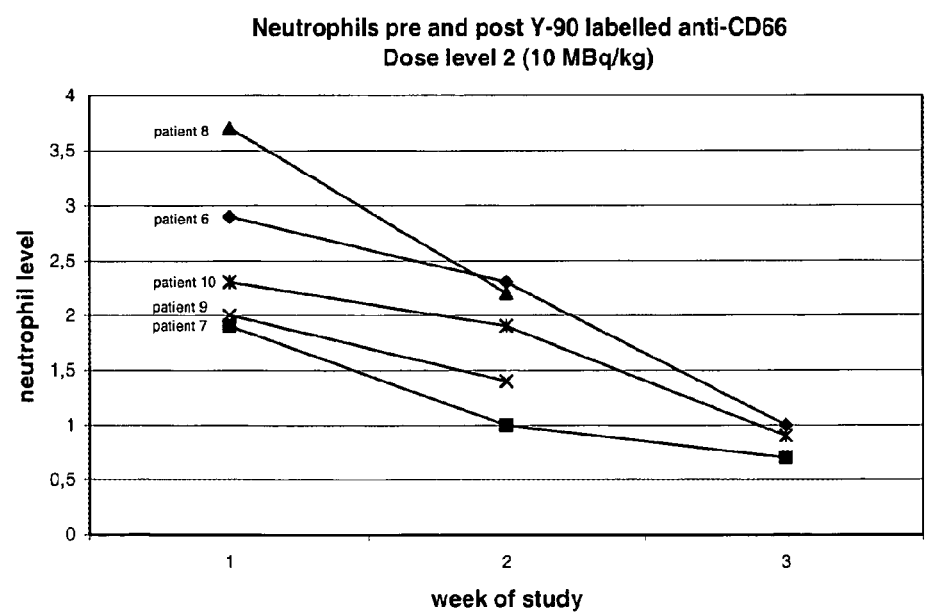

FIG. 3  *Platelet count pre and post Y-90 labelled anti- CD66 Mab*
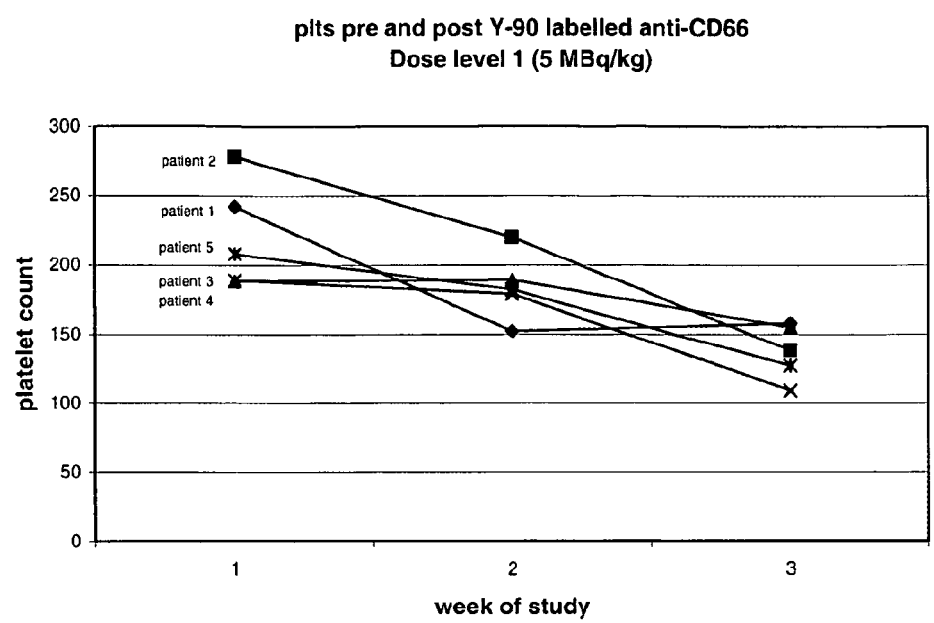
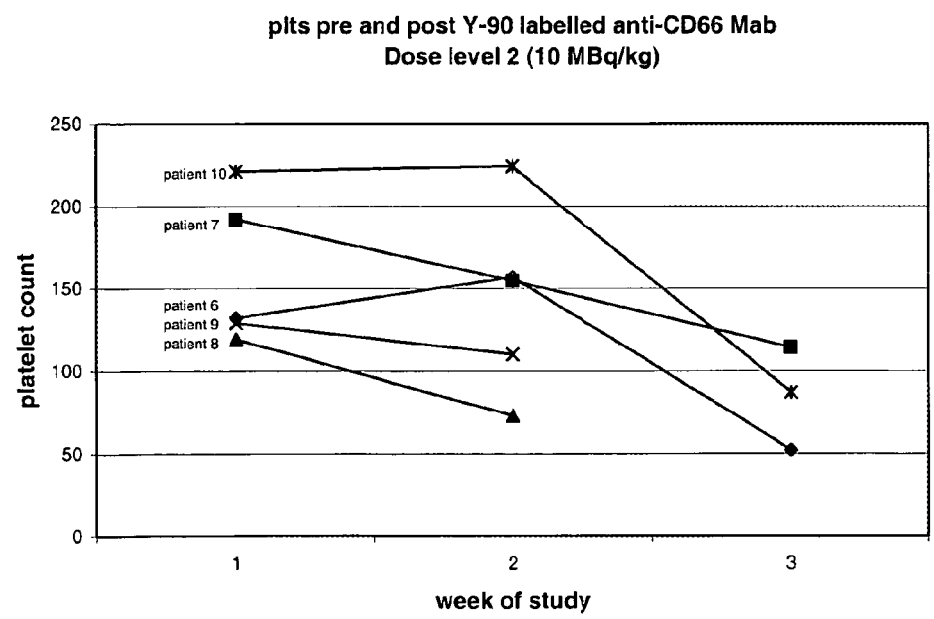

FIG. 4a    Pharmacokinetics of $^{111}$In-labelled anti-CD66 MAb
Blood time-activity curves for patients 1–12.
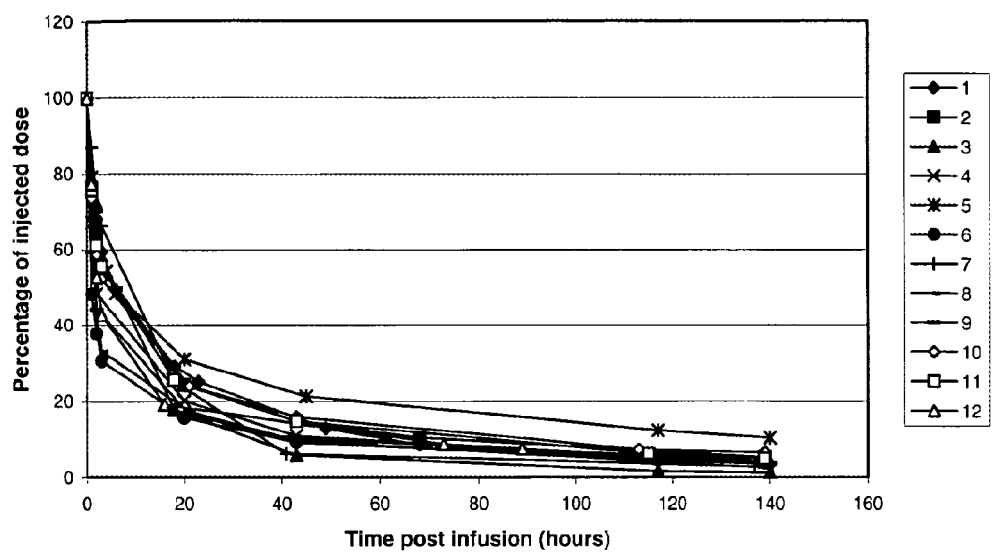
FIG. 4b    Early blood time-activity curves In-111
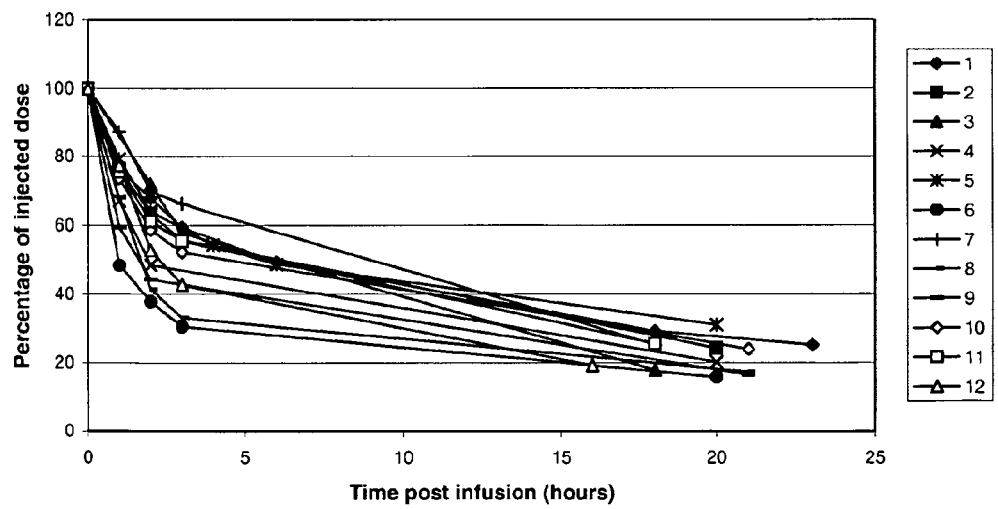
Time-activity curves for blood $^{111}$In activity in patients 1–12 show a similar biphasic curve. Extrapolation from the initial part of each curve allows the derivation of $T_{½}\alpha$, from the second part of the curve, $T_{½}\beta$.

FIG. 5

Whole body images

Anterior    Posterior

Whole body gamma camera images, anterior and posterior, 24 hours post infusion.

Note $^{111}$In-activity virtually completely associated with areas of red marrow and spleen. Little activity seen in the region of the liver.

No other organ images (such as kidneys) are apparent.

The $^{111}$In standard is visible at the bottom of the patient image.

FIG. 6   Cross-sectional image created from thoracic SPECT scans
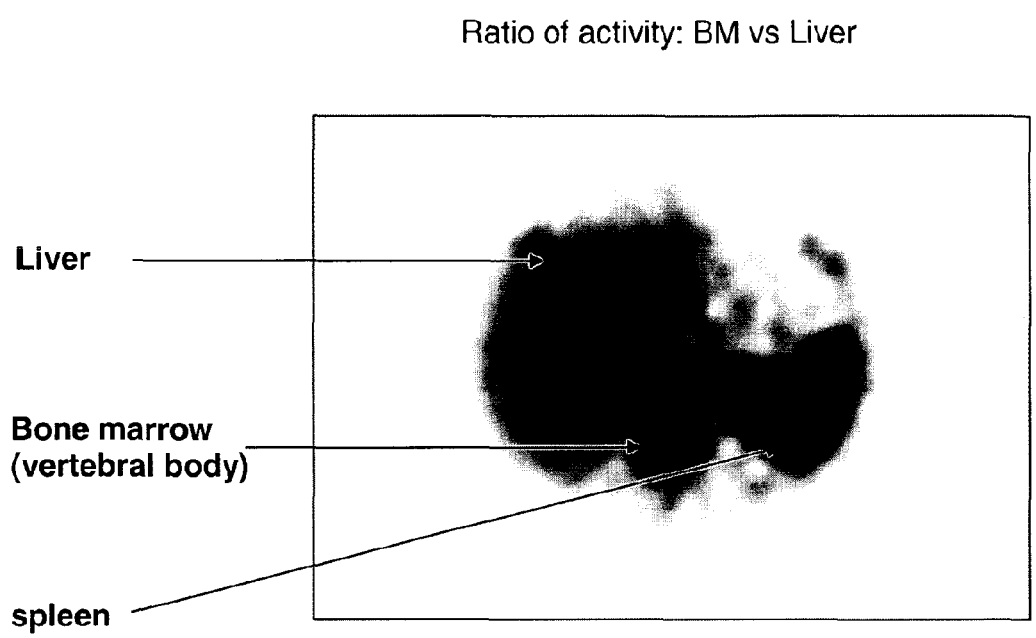
WITHOUT ANY CORRECTIONS FOR PARTIAL VOLUME EFFECT AND MARROW CELLULARITY, THE RATIO OF CUMULATED ACTIVITY PER 1ML OF TISSUE BETWEEN RED MARROW AND LIVER IS APPROXIMATELY 4:1 IN THIS PATIENT.

FIG. 7    Sequential whole body images
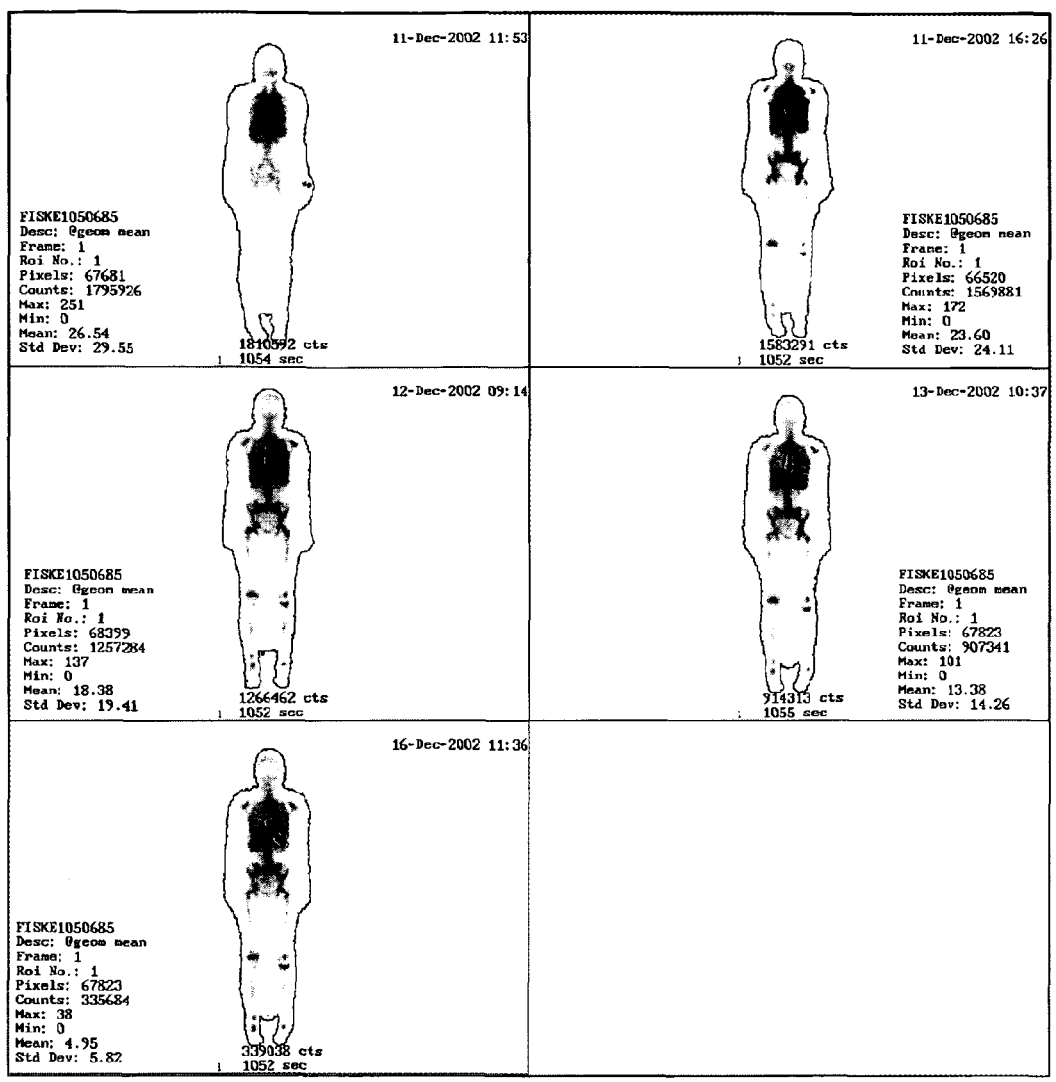
At 1 hour post infusion mainly blood pool activity is seen.
After 5 hours activity accumulates in the red marrow.
Activity remains in BM with no significant redistribution.
Note also increased uptake in right knee.

FIG. 8
Whole body $^{111}$In activity over 7 days in 2 patients
Patient 4
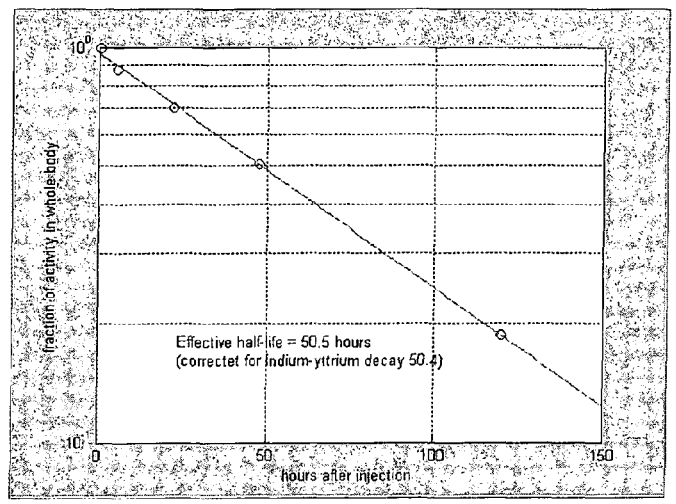
Patient 6
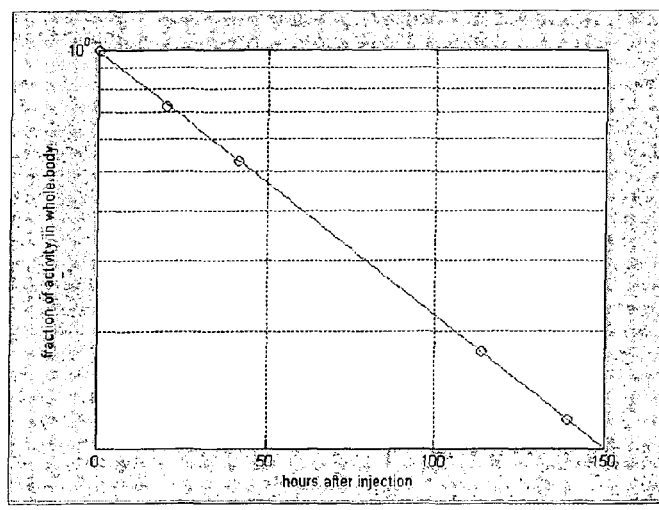
Results from different patients are very consistent indicating predictable dosimetry from initial organ distributions.

Representative plots from patients with multiple myeloma, demonstrating expression of CD66 on CD138/CD38 dual staining cells.

Graph of administered yttrium-90 activity (as MBq) vs estimated BM dose (Gy)

There is a linear relationship between the administered radiation dose and the dose delivered to the BM. This suggests that in the future individual patient dosing may be possible from a single early gamma image.

Table 1            Organ dosimetry

| Patient | Y-90 dose infused MBq | Organ dose estimates | | | | | |
|---|---|---|---|---|---|---|---|
| | | Bone Marrow | | Liver | | Spleen | |
| | | mGy/MBq | Gy | mGy/MBq | Gy | mGy/MBq | Gy |
| 1 | 550 | 10.1 | 5.6 | 3.4 | 1.9 | 4.9 | 2.7 |
| 2 | 425 | 10.0 | 4.3 | 2.3 | 1.0 | 14.6 | 6.2 |
| 3 | 385 | 7.7 | 3.0 | 5.0 | 1.9 | 1.5 | 0.6 |
| 4 | 455 | 11.7 | 5.3 | 2.4 | 1.1 | 6.9 | 3.1 |
| 5 | 275 | 7.6 | 2.1 | 3.8 | 1.0 | 4.3 | 1.2 |
| 6 | 815 | 9.6 | 7.9 | 1.6 | 1.3 | 8.3 | 6.8 |
| 7 | 1000 | 9.9 | 9.9 | 0.8 | 0.8 | 1.7 | 1.7 |
| 8 | 818 | 7.5 | 6.2 | 1.9 | 1.6 | 11.1 | 9.1 |
| 9 | 560 | 12.9 | 7.2 | 1.9 | 1.1 | 9.9 | 5.5 |
| 10 | 800 | 13.1 | 10.5 | 2.3 | 1.8 | 8.5 | 6.7 |
| 11 | 1375 | 9.6 | 13.2 | 2.4 | 3.3 | 6.2 | 8.5 |
| 12 | 1550 | 8.2 | 12.8 | 1.9 | 2.9 | 4.1 | 6.4 |
| 13 | 1700 | 12.0 | 20.0 | 2.0 | 3.5 | 8.2 | 14.2 |
| 14 | 1500 | 7.7 | 11.5 | 3.8 | 5.7 | 15.0 | 22.5 |
| 15 | 1450 | 10.8 | 15.7 | 2.0 | 2.9 | 7.6 | 11.1 |
| 16 | 2250 | 12.6 | 28.4 | 2.8 | 6.3 | 3.5 | 7.9 |
| 17 | 2510 | 8.9 | 22.2 | 3.7 | 9.2 | 5.3 | 13.3 |
| 18 | | | | | | | |
| 19 | 2325 | 7.3 | 16.9 | 2.1 | 4.8 | 7.9 | 18.4 |
| 20 | 2175 | 13.7 | 29.8 | 1.5 | 3.3 | 7.4 | 16.0 |

Organ dosimetry is expressed as mGy per infused MBq $^{90}$Y as determined from sequential gamma imaging of areas of interest and SPECT scans. Results analysed using MIRDOSE 3 to generate dose estimates of liver and spleen and from at least 2 sites of red marrow (lumbar vertebral body and pelvis).

FIG. 11

Table 2: Arithmetic mean and SD for organ dose and absorbed dose at each $^{90}$Y dose level.

| $^{90}$Y dose | Bone marrow | | Liver | | Spleen | |
|---|---|---|---|---|---|---|
| MBq/kg | mGy/MBq | Gy | mGy/MBq | Gy | mGy/MBq | Gy |
| 5 | 9.63 ± 2.1 | 4.12 ± 1.6 | 3.38 ± 1.1 | 1.40 ± 0.4 | 6.44 ± 5.0 | 2.76 ± 2.2 |
| 10 | 11.6 ± 1.9 | 9.14 ±1.6 | 1.69 ± 5.4 | 1.3 ± 0.4 | 7.75 ± 4.2 | 5.96 ± 2.7 |
| 25 | 10.25 ± 0.9 | 15.56 ± 2.0 | 2.41 ± 0.8 | 3.66 ± 1.2 | 8.22 ± 4.1 | 12.55 ± 6.3 |
| 37,5 | 10.61 ± 3.0 | 24.32 ± 4.3 | 2.5 ± 0.9 | 7.75 ± 2.1 | 6.03 ± 2.0 | 13.9 ± 4.5 |
| Overall | 10.05 ± 2.1 | - | 2.51 ± 1.0 | - | 7.21 ± 3.7 | - |

FIG.12

Toxicities.

Table 3:

| Organ | | |
|---|---|---|
| Haematological:‡ | | 20/20 grade 3 - 4 |
| Gastro-intestinal | | |
| | Mucositis: | 8/20 grade 1 |
| | | 6/20 grade 2 |
| | | 6/20 grade 3 |
| | Diarrhoea: | 15/20 grades 1 - 2 |
| | Liver | 1/20 grade 3* |
| Cardiovascular | | 1/20 grade 2** |

NB No infusional toxicities.

‡ Haematological toxicities grades 1-4 documented following infusion of Y-90 labelled anti-CD66 as shown in graphs of peripheral blood counts (figures 1, 2 and 3) increasing with radiation dose. Predictable grade 3-4 haematological toxicity in all patients after standard conditioning therapy.

*1 patient experienced raised bilirubin, secondary to other agents; resolved on withdrawal of these drugs (norethisterone and itraconazole)

**1 patient experienced transient asymptomatic atrial fibrillation and abnormal thyroid function tests indicative of hyperthyroidism (elevated T4, low TSH). Resolved after one month.

FIG. 13

Engraftment.

Table 4: Time to peripheral blood total white cell, neutrophil and platelet recovery (in days).

| Patient | Engrafted Y/N | WBC > 1.0 | Neuts > 0.5 | Plts > 50 |
|---|---|---|---|---|
| 1 | Y | 20 | 21 | 14 |
| 2 | Y | 12 | 12 | 15 |
| 3 | Y | 12 | 12 | 15 |
| 4 | Y | 14 | 16 | 13 |
| 5 | Y | 12 | 11 | 15 |
| 6 | Y | 11 | 12 | 10 |
| 7 | N | 55 | 55 | N/A |
| 8 * | Y | 17 | 19 | 11 |
| 9 * § | Y | 26 | 22 | 22 |
| 10 | Y | 15 | 15 | 14 |
| 11 | Y | 9 | 9 | 12 |
| 12 | Y | 12 | 12 | 12 |
| 13 | Y | | | |
| 14 | Y | | | |
| 15 | Y | | | |
| 16 | Y | | | |
| 17 | Y | | | |
| 18 | Y (delayed) | | | |
| 19 | Y | | | |
| 20 | Y | | | |
| Arithmetic means ± 1 SD | - | 17.9 ± 12.6 | 18.0 ± 12.4 | 13.9 ± 3.2 |

* Allogeneic stem cell transplant.
§ Bone marrow as stem cell source.

FIG. 14

Table 5:   Clinical Responses.

| Radiation Level | Patient | Malignancy / Status at transplantation | | Status at follow up in October 2005 |
|---|---|---|---|---|
| Radiation Level 1 5 MBq/kg bw | 001 | MM | PR | PR |
| | 002 | MM | PR | PR |
| | 003 | MM | PR | CR |
| | 004 | MM | PR | PR |
| | 005 | MM | PR | PR |
| Radiation Level 2 10 MBq/kg bw | 006 | MM | CR | CR |
| | 007 | MM | PR | PR |
| | 008 | AML | CR mini-allo | CR |
| | 009 | AML | CR mini-allo | CR |
| | 010 | MM | PR | CR |
| Radiation Level 3 25 MBq/kg bw | 011 | MM | CR | CR |
| | 012 | MM | PR | CR |
| | 013 | MM | PR mini-allo | CR |
| | 014 | MM | CR mini-allo | CR |
| | 015 | MM | PR | CR |
| Radiation Level 4 37.5 MBq/kg bw | 016 | MM | PR | CR |
| | 017 | MM | PR | CR |
| | 018 | MM | PR | PR |
| | 019 | MM | PR | Too soon to assess |
| | 020 | MM | PR | Too soon to assess |

MM :   multiple myeloma           PR :   partial remission
AML :  acute myeloid leukemia     CR :   complete remission

FIG. 15

IMMUNOCONJUGATE FOR HUMAN CD66 FOR THE TREATMENT OF MULTIPLE MYELOMA AND OTHER HAEMATOLOGICAL MALIGNANCIES

This application is the U.S. National Phase entry under 35 U.S.C. §371 and claims the benefit of International Application No. PCT/EP2006/011533, filed Nov. 30, 2006, which claims the benefit of U.S. Provisional Application No. 60/740,647, filed Nov. 30, 2005.

The present invention relates to the use of radioimmunoconjugates for the treatment of haematological malignancies, particularly multiple myeloma.

BACKGROUND OF THE INVENTION

Multiple myeloma comprises 1% of all cancers, and accounts for 10% of haematological malignancies. The median age at diagnosis is 60-65 years; <2% of myeloma patients are <40 years old at diagnosis.

The results of current treatments available for patients with symptomatic multiple myeloma are disappointing. The median survival is <3 years and the prospects for survival at 10 years are poor with conventional chemotherapy. Initial treatment with intermittent cycles of melphalan and prednisolone has a median duration of response of only twenty-four months and median survival of approximately three years. Consistently in clinical trials less than 10% of patients survive more than 10 years from diagnosis and there are very few long-term survivors. A number of combination chemotherapy regimens have been used and although higher response rates have been demonstrated there has been little impact on the duration of survival. High dose therapy followed by autologous bone marrow or peripheral blood stem cell rescue (AutoPBSCT) increases the response rate, disease free survival and overall survival but the majority of patients relapse within five years. The origin of cells causing relapse in these patients is not known but must arise either from the re-infusion of tumour cells contaminating autologous material or from inadequate elimination of disease by the conditioning regimen or a combination of the two. Increased tumour reduction in vivo could in theory be possible by further increasing the conditioning therapy. This has been tested in a number of studies using additional chemotherapeutic agents or with the addition of external beam or high-voltage total body radiotherapy as total body irradiation. However, intensification of conditioning therapy has been associated with significant increase in toxicity.

Frequently used first line conventional chemotherapy are combinations of up to 4 cytotoxic drugs such as doxorubicin, carmustine, cyclophosphamide, dexamethasone, etoposide, melphalan, (methyl)prednisolone, vincristine and idarubicin all of which are supplemented with bone protecting agents like bisphosphonates (Clodronate etc). However this treatment results rarely in complete remissions (CR) and long term remissions are rare.

Therefore, autologous stem cell transplantation (ASCT) was introduced as second line treatment of symptomatic MM patients. Various conditioning regimens such as high dose melphalan (HDM), HDM in combination with total body irradiation (TBI), HDM in combination with busulphan, low dose melphalan in combination with cyclophosphamide followed by TBI and HDM in combination with etoposide followed by TBI were clinically investigated.

HDM (200 mg/m$^2$) followed by ASCT has substantially increased the frequency of remission and has prolonged progression free survival (PFS) and overall survival (OS) being established now as the standard of care for treatment of symptomatic MM (Terpos E. et al., Expert Opin. Pharmacother., 2005, 6 (7): 1127-1142).

As third line setting thalidomide, bortezomib and others are used to further improve treatment. Furthermore, in a variety of studies experimental drugs such as anti-angiogenic compounds, histone deacetylase inhibitors, metalloprotease inhibitors, farnesyltransferase inhibitors, heat shock protein inhibitors and BCL2 antisense oligonucleotides are being evaluated.

The toxicity associated with further dose escalation has led to the development of tandem autologous transplants which allow the delivery of treatment intensification with less toxicity than the equivalent treatment in a single transplant event. The role of tandem stem cell transplantation remains undecided.

A feature of disease progression in myeloma is the appearance of chemotherapy resistance, in part due to the expression of the multiple-drug resistance mediated by p-glycoprotein, multi-drug resistance related protein or the major vault protein. New treatment strategies directed at the malignant cell population need to be developed, particularly that destroy malignant cells by mechanisms different to systemic chemotherapy. Therapeutic strategies that exploit the inherent radiosensitivity of malignant plasma cells while reducing the non-specific toxicity of external beam irradiation have been tested; these include total marrow irradiation in combination with busulphan and cyclophosphamide or targeted radiotherapy using radiolabelled bone seeking agents. Total marrow irradiation is technically difficult and in practice is a form of TBI with modified organ shielding, 90% of lung and liver were shielded (9 Gy in 6 fractions) and separate electron beam treatment given to rib areas protected from TBI. Overall response rates were good with 39/89 (44%) patients achieving CR and 50/89 (56%) a PR. In patients with de novo myeloma the CR rate was higher at 48%. However toxicity to non-haematopoietic tissues were high with 68/89 (76%) experiencing gastrointestinal toxicity grade III-IV. Durations of stay in hospital were also longer than for high dose melphalan due to the long (12 day) pre-treatment before stem cell infusion.

A number of radioimmunoconjugates (RIC) using monoclonal antibodies selective for haematopoietic antigens such as CD45, CD33, CD20, CD19 and CD66 have been the subject of investigations for bone marrow conditioning before transplantation in haematological malignancies such as acute lymphoblastic leukemia (ALL), acute myeloid leukemia (AML) and transformed myelodysplasia (MDS), (Matthews D. et al., Blood, 1999, 94: 1237-1247; Jurcic J G, Cancer Biother Radiopharm., 2000, 15: 319-326; Bunjes D. et al., Blood, 2001, 98: 565-572). RIC was applied in addition to standard conditioning regimens to evaluate their efficacy in a clinical setting. However, most of these radioimmunoconjugates show uptake in non-haematopoietic organs such as the liver and kidneys. The cause of this non-target uptake of radioimmunoconjugate is multifactoral and includes specific and non-specific uptake and instability of the immunoconjugate in vivo. This non-haematopoietic uptake limits the amount of immunoconjugate that can be administered, thus limiting their potential as targeting agents, reducing effective radiation dose delivered to the bone marrow. Consequently, despite a promising targeting effect on the tumor mass and bone marrow, the applied RICs show severe dose limiting toxicity in liver, lung and kidneys. This dose limiting toxicity may be due to the selectivity of the antibodies used and/or the stability of the attached radiolabel (e.g as observed using the $^{188}$Re labelled reduced molecule of anti-CD66 MAb studied by Bunjes et al.).

Thus, there is a need to provide further improved therapeutic procedures for the treatment of haematological disorders.

Unexpectedly, we have found that targeted radioimmunotherapy in bone marrow conditioning using a RIC consisting of monoclonal antibody BW 250/183 selective for CD66 (anti-CD66 MAb) radiolabelled with $^{90}$Y leads to complete remission in several cases of multiple myeloma.

A subject matter of the present application is the use of a radioimmuno-conjugate (RIC) for the manufacture of a medicament for the administration in the therapy of a haematological malignant disorder, particularly in a human patient, wherein the RIC comprises a CD66-binding component and a radionuclide.

The haematological malignant disorder may be a leukemia, which may be selected from multiple myeloma (MM), acute lymphoblastic leukemia (ALL), acute myeloid leukemia (AML), myelodysplastic syndrome (MDS), chronic myeloid leukemia (CML), chronic lymphocytic leukemia (CLL) and lymphoma. More particularly, the haematological malignant disorder is multiple myeloma.

The therapy may comprise administration of radionucleotides suitable for imaging and/or therapeutic irradiation of bone marrow as well as tumor cells. The RIC administration is preferably a conditioning regimen in combination with further therapeutic measures as explained in detail below.

The radionuclide of the RIC may be a therapeutically effective radionuclide, i.e. a radionuclide which is suitable for the treatment of haematological malignant disorders by irradiation. For example, the therapeutically effective radionuclide may be yttrium-90 ($^{90}$Y), iodine-131 ($^{131}$I), samarium-153 ($^{153}$Sm), holmium-166 ($^{166}$Ho) rhenium-186 ($^{186}$Re), rhenium-188 ($^{188}$Re) or another β- or β/γ-emitting radionuclide, or may be an α-emitter such as astatine-211 ($^{211}$At), bismuth-212 ($^{212}$Bi), bismuth-213 ($^{213}$Bi) or actinium-225 ($^{225}$Ac).

The radionuclide of the RIC may also be an imaging radionuclide, i.e. a radionuclide which is suitable for monitoring and/or determining pharmacokinetics of the RIC. For example, the imaging radionuclide may be indium-111 ($^{111}$In), iodine-131 ($^{131}$I) or technicum-99m ($^{99m}$Tc).

In an especially preferred embodiment the invention encompasses determining the therapeutically effective dose of a therapeutic RIC prior to administration. This determination may be carried out individually for a subject to be treated, or for a group of subjects, e.g. based on the severity or progression of the disease. For example, the invention may comprise the administration of an RIC comprising an imaging radionuclide and a subsequent administration of a RIC comprising a therapeutically effective radionuclide. By means of first administering an imaging RIC, the effective dose of the subsequently administered therapeutic RIC may be individually determined and/or adjusted for a respective subject, e.g. a human patient. In this embodiment, the CD66-binding component of the imaging RIC and the therapeutic RIC is preferably identical, at least with respect to the CD66-binding specificity and/or affinity.

It should be noted, however, that administration of an imaging RIC prior to administration of a therapeutic RIC might not be necessary, if sufficient patient data has been collected, e.g. in a database, to determine a therapeutically active amount of the RIC. Thus, a further preferred embodiment of the invention comprises determining a therapeutically effective dose of an RIC by evaluating pre-existing data, e.g. from a database.

The CD66-binding component is preferably a polypeptide comprising at least one antibody binding domain, for example an antibody, particularly a monoclonal antibody, a chimeric antibody, a humanized antibody, a recombinant antibody, such as a single chain antibody or fragment thereof, e.g. proteolytic antibody fragments such as Fab-, Fab'- or F(ab)$_2$-fragments or recombinant antibody fragments, such as single chain Fv-fragments.

The CD66-binding component may also be a fusion polypeptide comprising at least one antibody binding domain and a further domain, e.g. an effector domain such as an enzyme or cytokine. Alternatively, the CD66-binding molecule may be an ankyrin or a scaffold polypeptide.

In a preferred embodiment, the CD66-binding component selectively binds to the human CD66 antigen or an epitope thereof, e.g. CD66a, b, c, d or e. In an especially preferred embodiment the CD66-binding component is the BW250/183 antibody. Murine, humanized and recombinant forms of this antibody are described in EP-A-0 388 914, EP-A-0 585 570 and EP-A-0 972 528, which are herein incorporated by reference.

The radionuclide is preferably linked to the CD66-binding component via a chelating agent, with the linkage preferably being a covalent linkage. More preferably the radionuclide is linked to the CD66-binding component via a structure of the formula

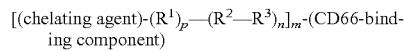

wherein n is 0 or 1,
m is 1 to 15,
p is 0 or 1,
$R^1$ and $R^3$ are independently selected from the group consisting of —NHCSNH—, —NHCONH—, —NHCOCH$_2$S—, —S—S—, —NH—NH—, —NH—, —S—, —CONHNH—, —SCH$_2$CH$_2$COONH—, —SCH$_2$CH$_2$SO$_2$—, —SCH$_2$CH$_2$SO$_2$NH—, —CONH—, —O—CH$_2$CH$_2$O—, —CO—, —COO—, —NH—O—, —CONHO—, —S—(CH$_2$)$_3$C(NH)NH—, —NH—COO—, —O— and

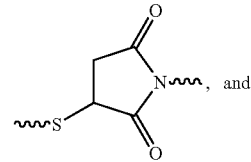

$R^2$ is selected from the group consisting of C1-C18 alkylen, branched C1-C18, —CH$_2$—C$_6$H$_{10}$—, p-alkylphenylene, p-phenylene, m-phenylene, p-alkyloxyphenylene, naphthylene, —[CH$_2$CH$_2$O]$_x$—, —[CH$_2$CH$_2$SOCH$_2$CH$_2$]$_x$—, —[CH$_2$CH$_2$SO$_2$CH$_2$CH$_2$]$_x$—, or —[NHCHR$_4$CO]$_y$—, wherein x is 1 to 200, y is 1 to 20, and wherein R$_4$ is selected from the group consisting of H—, Me-, HSCH$_2$—, isopropyl, but-2-yl, CH$_3$SCH$_2$CH$_2$—, benzyl, 1H-indol-3-yl-methyl, HOCH$_2$—, HOOCCH$_2$—, CH$_3$CH(OH)—, HOOCCH$_2$CH$_2$—, 4-hydroxybenzyl, H$_2$NCOCH$_2$—, H$_2$NCOCH$_2$CH$_2$—, 2-guanidinoethyl, 1H-imidazol-5-yl-methyl and 2-methylprop-1-yl.

For example, the chelating agent may be selected from the group consisting of diethylenetriaminepentaacetic acid (DTPA), 1,4,7,10-tetraazacyclododecane-N,N",N",N"'-tetraacetic acid (DOTA), 1,4,8,11-tetraazacyclotetradecane-N,N',N",N"'-tetraacetic acid (TETA), 1,4,7-triazonane-N,N',N"-triacetic acid (NOTA), 2,2'-(2-(((1S,2S)-2-(bis (carboxymethyl)amino)cyclohexyl)-(carboxymethyl) amino)ethylazanediyl) diacetic acid (cyclohexano-DTPA), 2,2'-(2-(((1R,2R)-2-(bis(carboxymethyl)amino)cyclohexyl)-(carboxymethyl)amino)ethylazanediyl)diacetic acid, 2,2'-(2-(((1S,2R)-2-(bis(carboxymethyl)amino)cyclohexyl)-(carboxymethyl)amino)ethylazanediyl)diacetic acid, 2,2'-(2-(((1R,2S)-2-(bis(carboxymethyl)amino)cyclohexyl)-(carboxymethyl)amino)ethylazanediyl)diacetic acid, 2,2',2'',2'''-(2,2'-(1S,2S)-cyclohexane-1,2-diylbis((carboxymethyl) azanediyl)bis(ethane-2,1-diyl))bis(azanetriyl)tetraacetic acid, 2,2',2'', 2'''-(2,2'-(1S,2R)-cyclohexane-1,2-diylbis((carboxymethyl)azanediyl)bis(ethane-2,1-diyl))bis(azanetriyl) tetraacetic acid, (1R)-1-benzyl-diethylenetriaminepentaacetic acid, (1S)-1-benzyl-diethylenetriaminepentaacetic acid, (2R)-2-benzyl-diethylenetriaminepentaacetic acid, (2S)-2-benzyl-diethylenetriaminepentaacetic acid, (2R)-2-benzyl-(3R)-3-methyl-DTPA, (2R)-2-benzyl-(3S)-3-methyl-DTPA, (2S)-2-benzyl-(3S)-3-methyl-DTPA, (2S)-2-benzyl-(3R)-3-methyl-DTPA, (2R)-2-benzyl-(4R)-4-methyl-DTPA, (2R)-2-benzyl-(4S)-4-methyl-DTPA, (2S)-2-benzyl-(4S)-4-methyl-DTPA, (2S)-2-benzyl-(4R)-4-methyl-DTPA, (1R)-1-benzyl-(3R)-3-methyl-DTPA, (1R)-1-benzyl-(3S)-3-methyl-DTPA, (1S)-1-benzyl-(3S)-3-methyl-DTPA, (1S)-1-benzyl-(3R)-3-methyl-DTPA, (1R)-1-benzyl-(4R)-4-methyl-DTPA, (1R)-1-benzyl-(4S)-4-methyl-DTPA, (1S)-1-benzyl-(4S)-4-methyl-DTPA, (1S)-1-benzyl-(4R)-4-methyl-DTPA, 2,2'-((1R,2R)-2-(((R)-2-(bis(carboxymethyl)amino)-3-phenylpropyl)(carboxymethyl)amino) cyclohexylazanediyl)diacetic acid, 2,2'-((1S,2S)-2-(((S)-2-(bis(carboxymethy(amino)-3-phenylpropyl) (carboxymethyl)amino)cyclohexylazanediyl)diacetic acid, 2,2'-((1R,2R)-2-(((S)-2-(bis(carboxymethyl)amino)-3-phenylpropyl)(carboxymethyl)amino) cyclohexylazanediyl)diacetic acid, 2,2'-((1S,2S)-2-(((R)-2-(bis(carboxymethyl) amino)-3-phenylpropyl)(carboxymethyl)amino) cyclohexylazanediyl)diacetic acid, 2,2'-((1R,2S)-2-(((R)-2-(bis(carboxymethyl)amino)-3-phenylpropyl) (carboxymethyl)amino)cyclohexylazanediyl)diacetic acid, 2,2'-((1S,2R)-2-(((S)-2-(bis(carboxymethyl)amino)-3-phenylpropyl)(carboxymethyl)amino) cyclohexylazanediyl)diacetic acid, 2,2'-((1S,2R)-2-(((R)-2-(bis(carboxymethyl) amino)-3-phenylpropyl)(carboxymethyl)amino)cyclohexylazanediyl)diacetic acid, 2,2'-((1R,2S)-2-(((S)-2-(bis(carboxymethyl)amino)-3-phenylpropyl) (carboxymethyl) amino)cyclohexylazanediyl)diacetic acid, (2S)-2-benzyl-1,4,7,10-tetraazacyclododecane-N,N',N'',N'''-tetraacetic acid, (2R)-2-benzyl-1,4,7,10-tetraazacyclododecane-N,N',N',N'''-tetraacetic acid, 6-benzyl-1,4,8,11-tetraazacyclotetradecane-N,N',N'',N'''-tetraacetic acid, 2-benzyl-1,4,7-triazonane-N, N',N''-triacetic acid, or a derivative thereof. In an especially preferred embodiment, isothiocyanato-benzyl-3-methyl-diethylenetriaminepentaacetic acid (ITC-2B3M-DTPA) is used as the chelating agent.

The administration of the therapeutic RIC for the treatment of human patients is preferably in a dose of ≥about 10 MBq/kg body weight (bw), preferably of ≥about 15 MBq/kg bw, more preferably of ≥about 20 MBq/kg bw, still more preferably of ≥about 25 MBq/kg bw, still more preferably of ≥about 30 MBq/kg bw and still more preferably of ≥about 35 MBq/kg bw. The RIC may be administered according to known methods, e.g. by infusion.

The RIC of the invention is preferably administered as conditioning regimen in a therapy which comprises additional measures, e.g. administering an antitumor agent, administering an immunosuppressive agent, and/or stem cell transplantation.

Examples of suitable antitumor agents to use in conjunction with RIC include chemotherapeutic agents such as melphalan, cyclophosphamide, (methyl) prednisolone, idarubicin, dexamethasone, etoposide, fludarabine, treosulphan, busulphan (oral or intravenous) alone or combinations of several, e.g. 2, 3, 4 of these agents optionally with bone protecting agents like bisphosphonates. Preferably, the chemotherapeutic agent is high dose melphalan, low dose melphalan or a combination of high dose melphalan or low dose melphalan optionally with other chemotherapeutics such as cyclophosphamide, fludarabine, busulphan and/or treosulphan. Further examples of suitable antitumor agents include antitumor antibodies such as Rituximab.

Examples of suitable immunosuppressive agents include antibodies such as Campath 1H, cyclosporin and rapamycin.

Stem cell transplantation comprises autologous and/or allogeneic stem cell transplantation.

Especially preferred therapeutic protocols, particularly for the therapy of multiple myeloma comprise the steps:
(a) administering an imaging RIC to the patient;
(b) administering a therapeutic RIC to the patient;
(c) administering at least one antitumor agent and/or an antitumor antibody to the patient; and
(d) transplanting autologous or allogeneic stem cells.

Preferably, step (c) comprises administering melphalan, e.g. high dose melphalan, a combination of fludarabine and antibody Campath 1H optionally with cyclophosphoamide and/or melphalan; cyclophosphamide and busulphan, cyclophosphamide in combination with total body irradiation, and fludarabine in combination with melphalan, busulphan and/or treosulphan. Specific stem cell transplantation conditioning regimens include administration of the following:

Cyclophosphamide 120 mg per m$^2$ and busulphan 16 mg per m$^2$ (or intravenous equivalent); cyclophosphamide 120 mg per m$^2$ and total body irradiation of any total dose, single or fractionated dose delivery; reduced intensity (also know as low intensity, 'mini-allogeneic transplant') regimens consisting of combinations of fludarabine and melphalan (doses 110-140 mg per m$^2$), fludarabine plus busulphan 8 mg per m$^2$ (oral or intravenous equivalent), fludarabine plus treosulphan.

Further, the invention shall be explained in more detail by the following examples.

BRIEF DESCRIPTION OF THE DRAWINGS

FIG. 4a shows blood activity curves for $^{111}$In-labelled anti-CD66 antibody for patients 1-12. The time-activity curves show a similar biphasic curve.

FIG. 4b illustrates an earlier part of the blood activity curves for $^{111}$In-labelled anti-CD66 antibody for patients 1-12. The immediate half-life and late half-life ($T_{1/2}\alpha$ and $T_{1/2}\beta$ respectively) of $^{111}$In activity were derived from this part of the curves. Extrapolation allowed the derivation of $T_{1/2}\alpha$, and $T_{1/2}\beta$.

FIG. 5 shows whole body gamma camera images, anterior and posterior, obtained 24 hours post infusion of the $^{111}$In-labelled anti-CD66 antibody. $^{111}$In-activity is virtually completely associated with areas of red marrow and spleen. Little activity seen in the region of the liver. No other organ images (such as kidneys) are apparent. The $^{111}$In standard is visible at the bottom of the patient image.

FIG. 6 is a cross-sectional image created from thoracic SPECT scans. Without correcting for partial volume effect and marrow cellularity, the ratio of cumulated activity per 1 ml of tissue between red marrow and liver is approximately 4:1 in this patient.

FIG. 7 shows sequential whole body gamma-scans (anterior only), indicating the radiation distribution, over the 5 days of imaging in patient 5. At 1 hour post infusion mainly blood pool activity is seen. After 5 hours activity accumulates in the red marrow. Activity remains in BM with no significant redistribution. Increased uptake of activity is also seen in right knee.

FIG. 8 shows the whole body $^{111}$In-activity over 7 days in two patients following infusion of $^{111}$In-labelled anti-CD66 antibody. Results from different patients are very consistent indicating predictable dosimetry from initial organ distributions.

FIG. 11: Table 1 organ dosimetry.

FIG. 12: Table 2 Arithmetic mean and SD for organ dose and absorbed dose at each $^{90}$Y dose level.

FIG. 13: Table 3 Toxicities.

FIG. 14: Table 4 Engraftment.

FIG. 15: Table 5 Clinical Responses.

EXAMPLE

Figure 1:
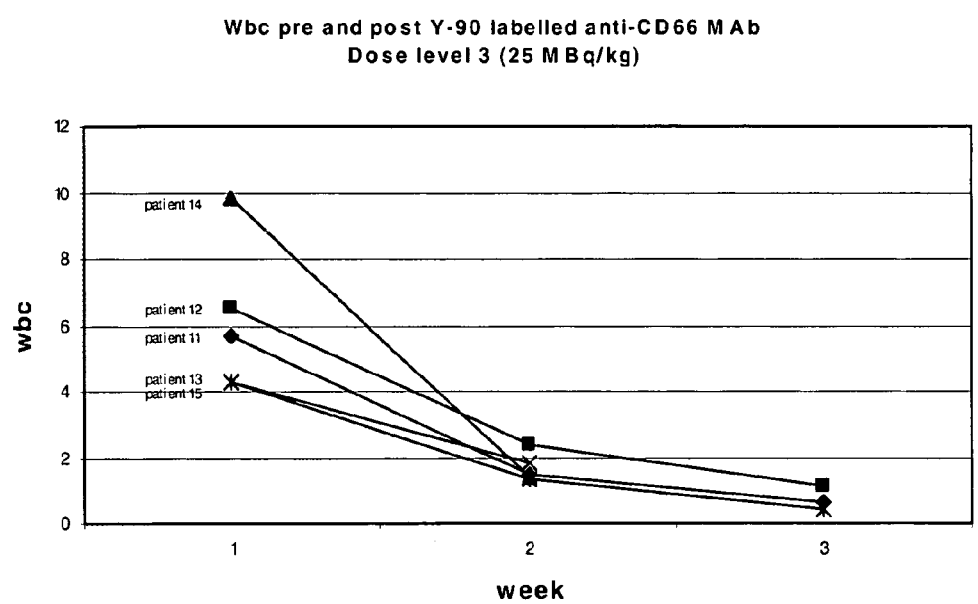
FIG. 1 illustrates the effects of administered $^{111}$In- and $^{90}$Y-labelled anti-CD66 antibodies on white cell counts. Blood samples were taken pre-infusion and on day 7 post infusion of $^{111}$In-labelled anti-CD66 MAb; pre-infusion and on days 7 and 12 post infusion of $^{90}$Y-labelled MAb. Administered $^{90}$Y dose levels were 5 MBq/kg, 10 MBq/kg, 25 MBq/kg, and 37.5 MBq/kg, respectively.
Figure 1:
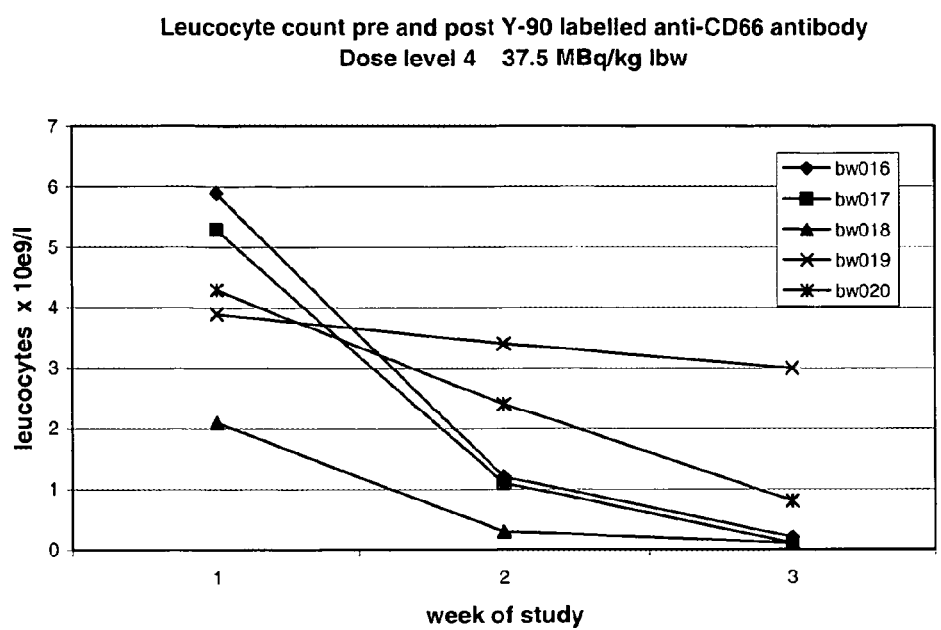

Aims and Objectives of the Study:
1. To determine the maximum tolerated dose (MTD) of targeted radiotherapy delivered by a mouse anti-CD66 MAb labelled with $^{90}$Y and determine the dose-limiting toxicity (DLT) in patients with haematological malignancies, preferentially MM, who are undergoing haematopoietic stem cell transplantation.
2. To determine the pharmacokinetics of $^{111}$In labelled anti-CD66 MAb in blood, urine and specific organs.
3. To develop a dosimetry model based on the pharmacokinetics of the labelled anti-CD66 Mab.

Study Design:
This was an open label, non-comparative, radiation dose escalation phase I study. Once the MTD had been established the study continued with the aim of determining the efficacy of additional radiation delivered by the monoclonal antibody. In the phase I study, the administered radiation dose was increased in four steps, with five patients at each radiation dose level.

Patients:
Patients with haematological malignancies defined as poor risk (including acute myeloid leukaemia in CR1 but with poor prognostic features or in >CR1 or in relapse; acute lymphoblastic leukaemia; transformed myelodysplasia, chronic myeloid leukaemia (accelerated phase or blast transformation), and multiple myeloma) and who were due to undergo a haematopoietic stem cell transplant procedure were asked to enter the study. Patients were in remission, partial remission or relapse.

Outline of Methodology:
Preparation of RIC
MAb BW250/183 (now anti-CD66 a, b, c) is a mouse IgG$_1$ which binds to an epitope shared by several membranes and protoplasm of the myeloid cells of granulocytopoiesis cluster of antigenic epitopes including those expressed by neutrophils.

The antibody does not demonstrate any antibody-dependent cell mediated cytotoxicity nor human complement mediated cytotoxicity.

$^{111}$In and $^{90}$Y are radiometals and do not directly bind to protein. To bind to proteins (antibody) a bifunctional chelating agent is required, radiolabelling is thus a two stage process. Firstly, the chelating agent is covalently linked to the antibody, via the amino-residues on lysine residues; this form is stable. Secondly, labelling with the radiometal, which is performed immediately before the use of the radiolabelled antibody. The conjugated antibody is stable in aqueous solution and may be stored frozen. The conjugated antibody can then be radiolabelled with the selected radiometal, within a few hours of infusion. Stability tests show that the labelled antibody retains >99% of original activity when stored at 4° C. for up to 6 hours.

The bifunctional chelating agent chosen for conjugation to the anti-CD66 MAb in this study was isothiocyanatobenzyl-3-methyl-diethylenetriaminepenta-acetic acid (ITC-2B3M-DTPA). A batch of anti-CD66 MAb was conjugated under GLP conditions. The product was tested for immunoreactivity, sterility, endotoxin level, conjugation efficiency, labelling efficiency and in vitro stability with $^{111}$In and $^{90}$Y. The conjugated antibody was also checked for multimerisation by HPLC and purity by SDS gel electrophoresis.

Aliquots of conjugated MAb BW250/183 were frozen in sterile single patient dose vials. The conjugated MAb BW250/183 has a batch number and each vial was given a unique identification number.

The conjugated anti-CD66 MAb was radiolabelled with tracer activity (approximately 185 MBq) of $^{111}$In suitable for imaging. The RIC was administered as a single slow infusion. The pharmacokinetics of the RIC was monitored by serial blood sampling, continuous urine collection and serial quantitative whole body and SPECT gamma-camera imaging. Radiation doses to specific organs were calculated from the planar and SPECT gamma-camera data. If the estimated radiation dose to the red marrow exceeded by 2-fold the dose received by a non-haematological organ then the patient received a second infusion of the anti-CD66 antibody, labelled with the therapeutic dose of $^{90}$Y. The starting radiation activity of $^{90}$Y-labelled anti-CD66 MAb was 5 MBq/kg body weight.

Administration of Labelled Anti-CD66 Mab:
For dosimetry/pharmacokinetics 2 mg of radiolabelled anti-CD66 MAb was infused. Blood samples, gamma imaging and urine collections were performed over the following 7 days. If favourable biodistribution and organ dosimetry was demonstrated the second infusion of 2 mg of RIC, labelled with a therapeutic dose of $^{90}$Y, was given.

All patients were treated as out-patients for both the imaging and therapy doses of radiation.

Study Parameters:
1) Pharmacokinetics of $^{111}$In-labelled anti-CD66 MAb as determined from serial blood samples, serial planar and SPECT gamma-camera imaging of selected organs.

2) The dose limiting toxicity of $^{90}$Y-labelled anti-CD66 MAb (radiation dose).
3) The maximum tolerated dose of radiation delivered by $^{90}$Y-labelled anti-CD66 Mab.

$^{90}$Y Dose Escalation:

There are four radiation dose levels with five patients at each level.

| | |
|---|---|
| 1$^{st}$ dose level | 5 MBq/kg (body weight) |
| 2$^{nd}$ dose level | 10 MBq/kg (body weight) |
| 3$^{rd}$ dose level | 20 MBq/kg (amended to 25 MBq/kg lean body weight) |
| 4$^{th}$ dose level | 30 MBq/kg (amended to 37.5 MBq/kg lean body weight) |

The $^{90}$Y dose for each patient in the first 2 levels was determined using 'real' body weight. In order to reduce inter-patient dose variation (due to extremes of body weight), a protocol amendment was made: for dose levels 3 and 4 the protocol was amended to use 'lean' body weight. In parallel the 3$^{rd}$ dose level was changed to 25 MBq per kg lean body weight, the 4th dose level as 37.5 MBq per kg lean body weight.

Conditioning Schedules:

Conditioning schedules were determined by the underlying disease indication and the type of transplant (autologous, allogeneic). The majority of patients (10 of 12) were receiving high dose melphalan as treatment for myeloma, two patients (patients 8 and 9) were due to undergo fully matched sibling allogeneic transplants for poor risk acute myeloid leukaemia. Targeted radioimmunotherapy using $^{90}$Y-labelled anti-CD66 was used in addition to the scheduled transplant conditioning.

Autologous Stem Cell Transplant:

For patients receiving HDM (200 mg per m$^2$ surface area) the following schedule was used:

| ACTION | TIME |
|---|---|
| Imaging and dosimetry ($^{111}$In-labelled anti-CD66 MAb) | Day −21 (range −21 to −20) |
| Infusion of therapeutic dose of $^{90}$Y-labelled anti-CD66 MAb | Day −14 |
| Review of patient | Day −8 |
| Infusion of HDM | Day −2 |
| Infusion of stem cells | Day 0 |

Allogeneic Transplant:

For patients receiving allogeneic transplants the following schedule was used:

| ACTION | TIME |
|---|---|
| Imaging and dosimetry ($^{111}$In-labelled anti-CD66 MAb) | Day −21 (range −21 to −20) |
| Infusion of therapeutic dose of $^{90}$Y-labelled anti-CD66 MAb | Day −14 |
| Admission of patient for "standard" conditioning schedule* | Day −9 |
| "Standard" conditioning | Day −8 to Day −1 |
| Infusion of allogeneic stem cells | Day 0 |

*patients 8 and 9 both received low intensity conditioning schedules consisting of fludarabine, cyclophosphamide and Campath 1H (patient 8) or fludarabine, melphalan and Campath 1H (patient 9). Targeted radiotherapy was used in addition to the established conditioning schedules.

Methods:
1) Effect of administered radiation on blood counts.
2) Blood activity curves.
3) Radiolabelled anti-CD66 MAb biodistribution.
4) Organ dosimetry.
5) Toxicity post infusion of $^{90}$Y-labelled anti-CD66 MAb.

Figure 2:
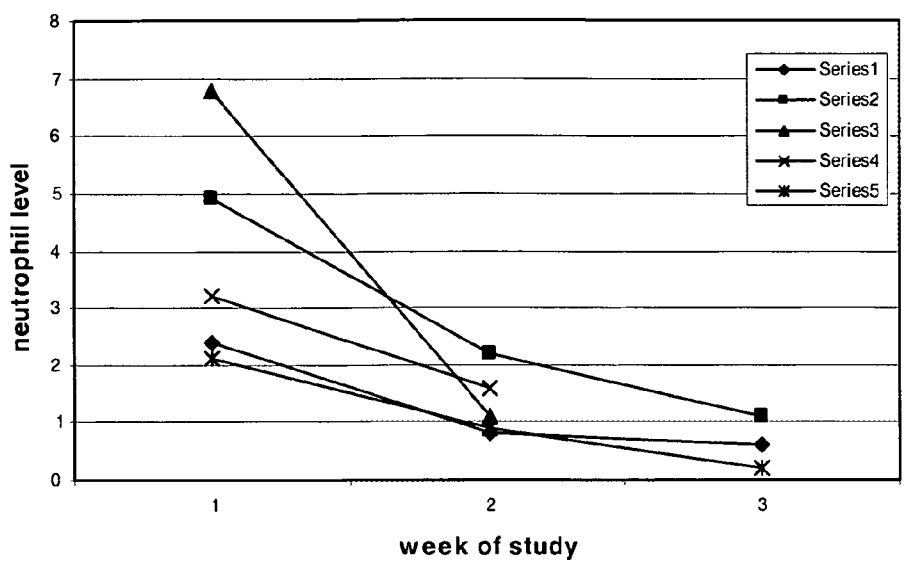
FIG. 2 illustrates the effects of administered $^{111}$In- and $^{90}$Y-labelled anti-CD66 antibodies on neutrophil counts. Blood samples were taken pre-infusion and on day 7 post infusion of $^{111}$In-labelled anti-CD66 MAb; pre-infusion and on days 7 and 12 post infusion of $^{90}$Y-labelled MAb. Administered $^{90}$Y dose levels were 5 MBq/kg, 10 MBq/kg, 25 MBq/kg, and 37.5 MBq/kg, respectively.
Figure 2:
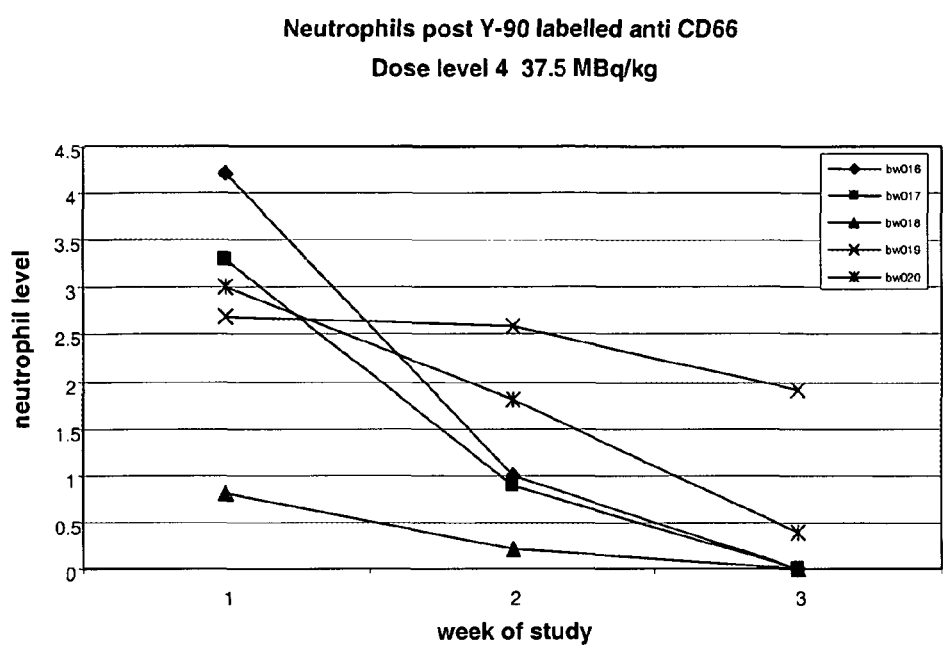
Figure 3:
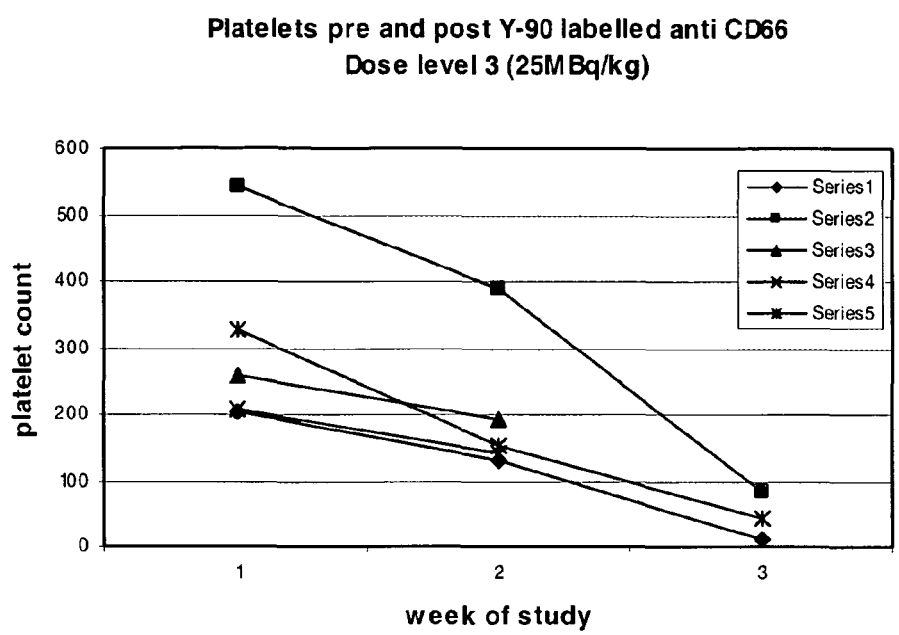
FIG. 3 illustrates the effects of administered $^{111}$In- and $^{90}$Y-labelled anti-CD66 antibodies on platelet counts. Blood samples were taken pre-infusion and on day 7 post infusion of $^{111}$In-labelled anti-CD66 MAb; pre-infusion and on days 7 and 12 post infusion of $^{90}$Y-labelled MAb. Administered $^{90}$Y dose levels were 5 MBq/kg, 10 MBq/kg, 25 MBq/kg, and 37.5 MBq/kg, respectively.
Figure 3:
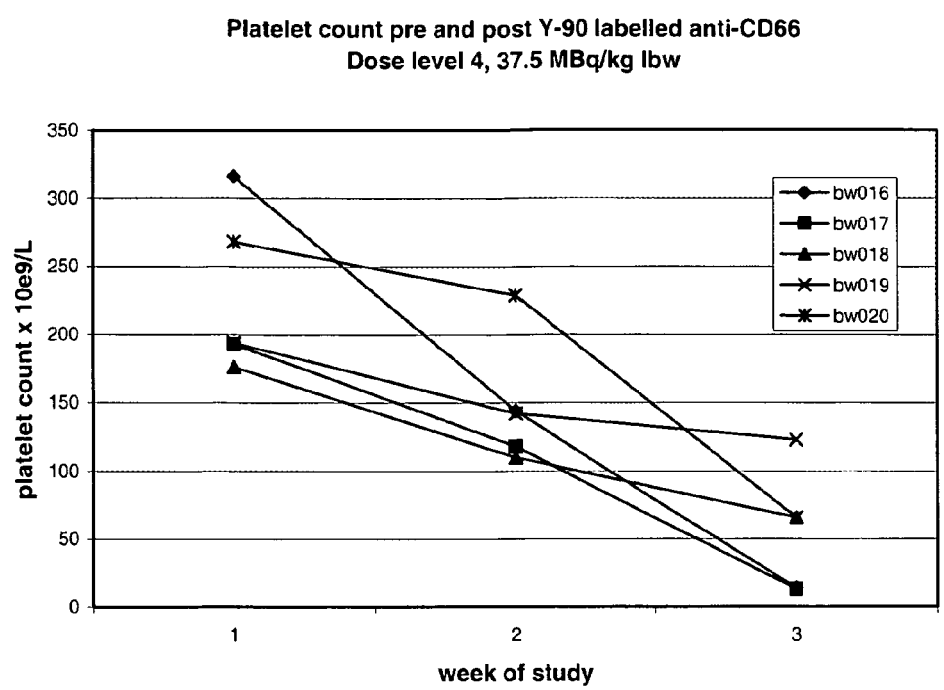

1. Effect of Administered Radiolabelled Antibody on Peripheral Blood Counts:

Blood samples were taken for full blood count and white cell differential pre-infusion and on day 7 post infusion of $^{111}$In-labelled anti-CD66 MAb; pre-infusion and on days 7 and 12 post infusion of $^{90}$Y-labelled MAb. The results of total white cell count (FIG. 1), neutrophil count (FIG. 2) and platelet count (FIG. 3) PBCs following $^{90}$Y-labelled anti-CD66 Mab are shown in FIGS. 1-3 for $^{90}$Y dose levels of 5 MBq/kg, 10 MBq/kg, 25 MBq/kg and 37.5 MBq/kg respectively.

2. Blood Activity Curves for $^{111}$In-Labelled Anti-CD66 MAb:

Whole blood samples were taken pre-infusion, immediately at the end of infusion (T=0) and 1, 2, 3, 4 hours and daily up to day 7 post infusion. A total of 7-9 samples were collected from each patient. Gamma-activity was determined on 1 ml aliquots in triplicate, all samples were analysed on the same day with $^{111}$In standards. A standard curve was plotted and gamma-activity converted into $^{111}$In activity of the blood samples using the standard curve. Results were expressed as percentage injected dose (% ID) and plotted against time in hours post infusion. Circulating total blood volumes for each patient were derived from standard tables (Hurley). The immediate half-life and late half-life ($T_{1/2}\alpha$ and $T_{1/2}\beta$ respectively) of $^{111}$In activity were derived from the curves. Results are shown in FIGS. 4a and 4b.

3. Radiolabelled Anti-CD66 MAb Biodistribution:

Targeting and organ biodistribution of infused $^{111}$In-labelled MAb was determined from serial whole body gamma-images taken on the day of infusion (day 1) and days 2, 3, 6 and 7 post. A dual-headed gamma camera (Genesys ADAC) was used with windows set for the characteristic peak $^{111}$In gamma photon energy levels. The camera was calibrated for each patient using a standard with a known activity of $^{111}$In. FIG. 5 shows anterior and posterior whole body images taken 24 hours after infusion for patient 4.

4. Organ Dosimetry:

For dosimetry investigations, patients received approximately 185 MBq of $^{111}$In-labelled anti-CD66 MAb by infusion over 15 minutes. Anterior and posterior whole body images were obtained on days 1, 2, 3, 6 and 7 after injection (day 1=day of infusion). From the whole body images, the pattern of activity distribution and clearance was assessed. Time-activity curves for the whole body were compared with blood activity.

SPECT studies were obtained on days 1, 2 and 6 or 7; SPECT of the thorax and pelvis provided images of anatomical sites of all important organs (liver, lungs, kidneys, red marrow, spleen). A typical SPECT scan image is shown in FIG. 6.

Organ dosimetry was calculated from quantification of reconstructed SPECT images. Counts in images were converted to activity using conversion factors from test objects measurements (Carlson phantom).

Time-activity curves were plotted and cumulated activity calculated from uptake at time zero U0 and effective clearance constant $\Delta$eff as Acum=U0/$\Delta$eff according to MIRD schema (Society of Nuclear Medicine). Absorbed dose D in Gy (Gray) was obtained by multiplying cumulated activity by appropriate S (mean dose per unit cumulated activity) values (MIRDOSE 3) as D=Acum×S.

For large organs such as liver, where distribution of activity is relatively homogeneous, using mean counts in a representative region of interest (ROI) was sufficient. Accurate quantification of bone marrow dose was affected by the apparent loss of counts in smaller regions (partial volume effect). This required correction using recovery coefficients obtained from experiments with test objects, of comparable sizes to skeletal regions containing red marrow. Estimating total marrow activity (and thus dose) from ROI analysis involves assumption of the proportion of active red marrow (cellular fraction) in the analysed samples (obtained from biopsy samples when available) as well as total volume of active red marrow. This was scaled according to lean body weight from reference data for males and females (Stabin 1996).

Another method for calculation of organ dosimetry involved the calculation of total activity in larger skeletal regions—e.g. spine or pelvis. From tabulated data (e.g. reference Man) percentage of total red marrow in these regions can be assumed and total marrow activity obtained. This does not require the knowledge of cellular fraction but the total volume of active red marrow must be assumed as above.

FIG. 7 shows the whole body gamma-scans (anterior only), indicating the radiation distribution, over the 5 days of imaging in patient 5.

FIG. 8 shows the whole body $^{111}$In-activity over the 7 day period after infusion of $^{111}$In-labelled antibody as a semi-log graph from which the effective biological half-life of the radiation was calculated.

5. Toxicity Post Infusion of $^{90}$Y-Labelled Anti-CD66 MAb

Toxicity data were collected and recorded following the administration of the therapeutic dose of targeted radiation, weekly up to 1 month post transplantation, then every month up to 3 months post transplant. NCIC Toxicity criteria were used.

Results:

Effect of Anti-CD66 MAb Targeted Radiotherapy on Blood Counts:

FIGS. 1, 2 and 3 shows the results of peripheral blood white cell, neutrophil and platelet count, respectively, pre and post $^{90}$Y-labelled anti-CD66 MAb infusion. 'Week 1' on the plots was the day of infusion, 'week 2' 7 days post and 'week 3' 12 days post and on the day of high dose therapy. Patients 8 and 9 received low intensity conditioning prior to allogeneic transplantation (for AML) and the results are censured at day 7, the start of the standard conditioning. It is clear from these results that the radiolabelled antibody infusion was associated with a marked fall in total white cell, neutrophil and platelet counts implying a significant myelo-suppressive effect of the radiation. The earlier infusion of the $^{111}$In-labelled anti-CD66 MAb for imaging and dosimetry did not result in any changes of the peripheral blood cellular components (data not shown) indicating that the fall was due to the effect of beta-radiation rather than the antibody itself. There may also be a dose effect on the degree of myelo-suppression, as shown by the rate of fall in counts and the nadir of the count. It is clear that at the highest radiation dose patients are neutropenic before standard chemotherapy had been administered.

$^{111}$In Activity in Whole Blood:

FIGS. 4a and 4b show the blood time-activity curves for all patients. The plotted blood activities show a similar pattern between patients, a biphasic curve, consistent with the sum of two exponential functions. In each patient an initial rapid fall in blood $^{111}$In activity (within 2 hours) was followed over the following 5-10 hours by a slower decrease. After 24 hours the decrease in activity was markedly slower, approximating to the physical half-life of the isotope.

The initial rapid fall occurs at the time of localisation of activity from the blood pool into the marrow, as shown by serial whole body gamma images (FIG. 7). From the early time-activity plots (FIG. 4b) the derived $T_{1/2}\alpha$ was 2.06+/−0.96 hours (range 0.9-3.4) and $T_{1/2}\beta$ 43 6.0+/−3.2 hours (range 4.0-9.0). $T_{1/2}\alpha$ is a function of biodistribution immediately following infusion and is influenced by the accessibility of the target antigen, avidity of the antibody and non-specific binding (if significant). The derived values for $T_{1/2}\alpha$ may be higher than the true values as blood samples were taken at only 1 hour time points immediately post infusion. To derive more accurate value for $T_{1/2}\alpha$ samples may need to taken more frequently within the first 2 hours post infusion.

Radiolabelled Anti-CD66 MAb Biodistribution

FIG. 5 shows the whole body gamma camera images, anterior and posterior, 24 hours following infusion of the $^{111}$In-labelled MAb (patient 5). An image of the axial skeleton and proximal long bones is seen, corresponding to sites of active bone marrow. The spleen is also visible but of note only a faint image corresponding to the liver is apparent. Nor are any other organs visible.

FIG. 6 is a SPECT scan image taken at the level of a lower thoracic vertebral body. Images of the vertebral body and the spleen can be clearly seen with strong associated gamma activity, as indicated by the arrows. A faint image of the liver can also be seen. Quantification of the gamma radiation shows a 4:1 ratio of activity between the vertebral marrow and liver.

This does not take into account any partial volume effects, which are likely to artificially reduce the gamma radiation quantification for small images such as the vertebral marrow, but will not effect the quantification of a large organ such as the liver.

FIG. 7 shows the whole body images of one patient taken over five days of imaging and dosimetry. Immediately after infusion (image 1) activity was seen in the blood pool (heart image), by 5 hours post infusion (image 2) activity was seen to have begun to accumulate in the marrow and spleen. Over the following 5 days (images 3, 4 and 5) activity remains predominantly in the marrow and spleen although a small increase in activity within the liver was apparent by 128 hours. From the sequential images and gamma radiation quantification the biological half-life of $^{111}$In was calculated to be approximately 50 hours. In this patient, the marrow image extended throughout the long bones, in particular an area of increased activity was seen in the right knee. This patient was receiving an autologous stem cell transplant after high dose melphalan as treatment for multiple myeloma, they were in a partial remission pre-transplant. The patient experienced pain in the right knee which resolved following the infusion of $^{90}$Y-labelled antibody. A plain X-ray of the knee failed to demonstrate any abnormality, however an MRI scan showed the presence of a small lytic lesion. This suggested the possibility that the antibody was accumulating not only in normal bone marrow but also in sites with heavy plasma cell infiltration. The possibility that CD66, described as a myeloid cell marker, may be expressed by mature plasma cells, was investigated by FACS analysis of bone marrow aspirates taken from patients with multiple myeloma:

Demonstration of CD66 Expression on Malignant Plasma Cells by Flow Cytometry

Diagnostic bone marrow aspirate samples from patients with suspected multiple myeloma were examined by multi-parametric flow cytometry in order to demonstrate and quantitate neoplastic plasma cells.

Washed bone marrow cells were incubated with standard primary panel of pre-titrated antibodies including a combination of anti-CD19 fluorescein isothiocyanate (FITC) (Pharmacia), anti-CD5 phycoerythrin (PE) (in house), anti-CD45 peridin chlorophyll protein (PerCP) (Becton Dickinson) and anti-CD38 allophycocyanin (APC) (Pharmacia). Samples were then treated with lysing solution to lyse erythrocytes under hypotonic conditions whilst preserving leukocytes, washed twice and acquired using a Becton Dickinson FACSXCalibur with CELLQuest software (BD Biosciences). Between 20.000 and 100.000 events were acquired and analysed per sample test. A gating strategy was used to optimise exclusion of contaminating events such as cellular debris and apoptotic bodies.

Marrow samples shown to contain a clear CD45 negative, CD19 negative, CD38 positive population, consistent with the presence of plasma cells, were then re-analysed (new aliquot) with a myeloma panel, consisting of an anti-CD38 APC, an anti-CD45 PerCP, and anti-CD138 PE (Diaclone) and the anti-CD66 (TheraPharm GmbH). As the anti-CD66 was a naked antibody (murine $IgG_1$), this was added to the sample for the myeloma panel analyst first, washed three times, then incubated with sheep anti-mouse IgG F(ab')$_2$ fragment conjugated to FITC (Pharmacia), again washed three times. Samples were then analysed using myeloma panel antibodies (anti-CD38 APC, anti-CD45 PerCP; anti-CD138 PE). Again, between 20.000 and 100.000 events were acquired and analysed per sample. CD66 positive cells were scored with CD38 or CD138.

Diagnostic samples from 12 patients with multiple myeloma have been analysed and all (100%) were found to have CD138/CD38 dual positive plasma cells which co-expressed CD66 with varying intensity.

Figure 9:
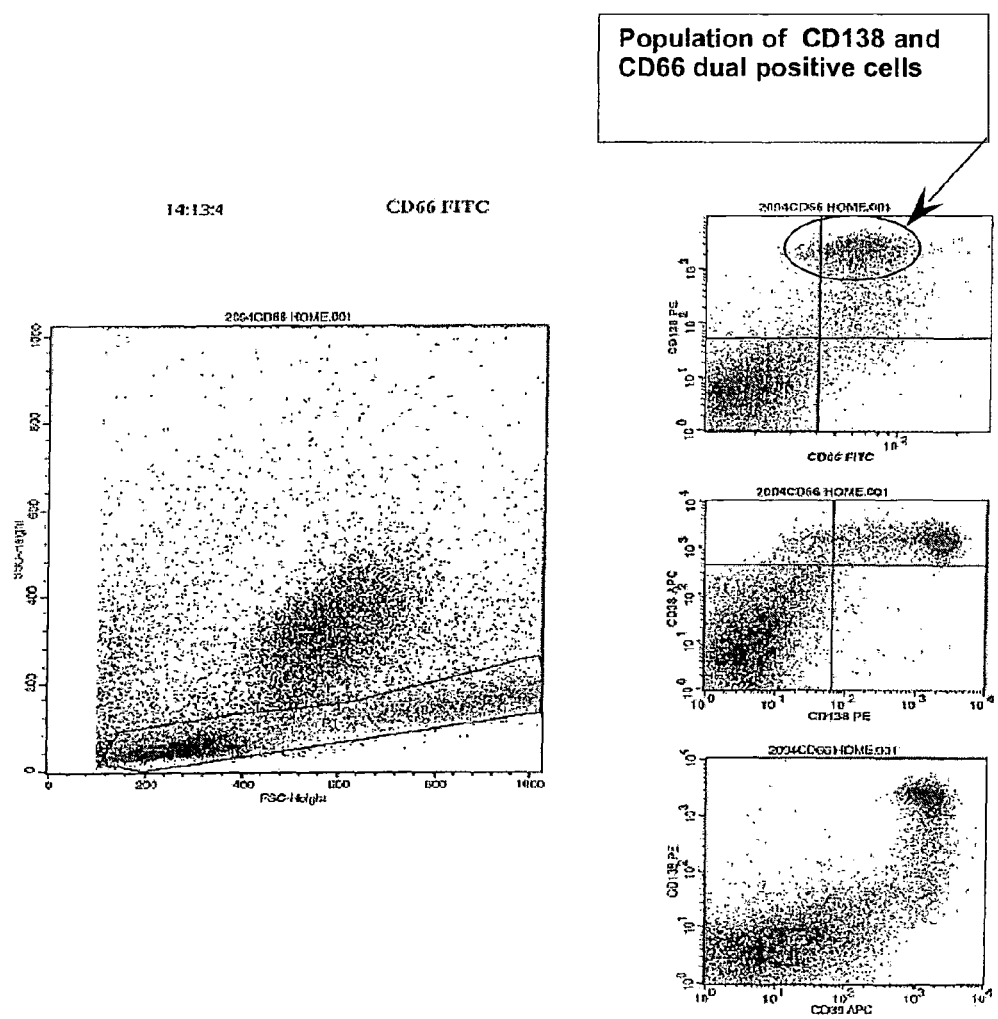
FIG. 9 shows representative FACS plots from patients with multiple myeloma, demonstrating expression of CD66 on CD138/CD38 dual staining cells.

FIG. 9 shows representative FACs plots for 3 different patients. Negative controls in which the anti-CD66 MAb was not added showed no FITC scored events.

The bone marrow of a normal individual was also examined and found to contain plasma cells which co-expressed CD19, CD138, CD38 and CD66 (data not shown).

Figure 10:
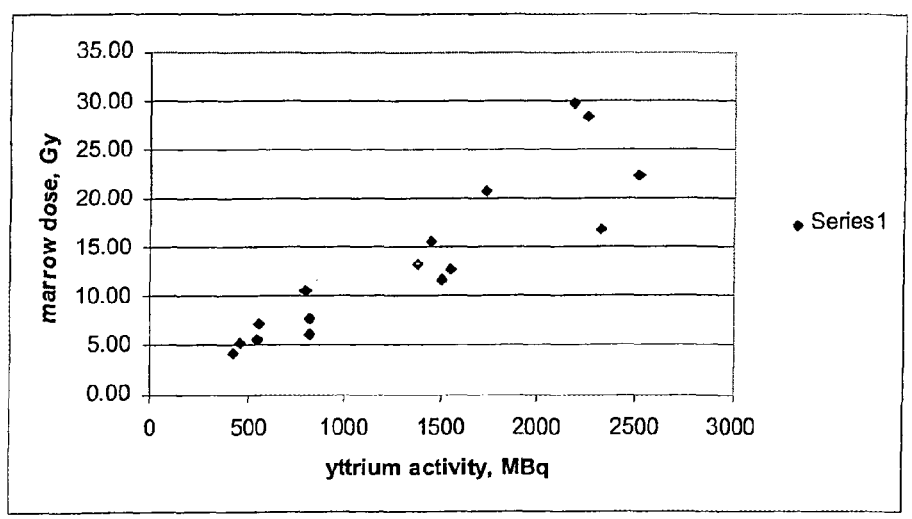
FIG. 10 is a graph of administered yttrium-$^{90}$ activity (as MBq) vs estimated BM dose (Gy).

Organ Dosimetry:

Table 1 shows the estimated radiation dose delivered to the bone marrow, liver and spleen expressed as milliGray (mGy) per megaBequerel (MBq) of infused $^{90}$Y-labelled anti-CD66 MAb and as Gray (Gy). The total activity of $^{90}$Y infused for each individual patient is shown in the second column. In this context, a linear relationship between the adminstered radiation dose and the dose delivered to the bone marrow is observed, as can be derived from the plot of FIG. 10. This result, on the other hand, suggests the possibility of individual patient dosing from a single early gamma image in the future.

In Table 2 the mean radiation dose as mGy/MBq and mean total dose in Gy is shown. The uptake of radiolabelled antibody by the marrow showed a high degree of consistency between patients, with a mean of 9.94+/−1.2 mGy/MBq (range 7.7-11.8 mGy/MBq). The uptake by the liver and spleen showed a wider variation between patients, 3.33+/−1.7 mGy/MBq (range 1.56-6.53) for the spleen and 1.4+/−1.24 mGy/MBq (0.705-4.99) for liver. The total radiation dose delivered to the bone marrow has a linear relationship to the total $^{90}$Y activity infused over the doses used. Mean radiation doses to the liver were substantially less than that received by the bone marrow or spleen. In addition, estimated radiation doses to other organs such as lung, kidneys, muscle, gut were all significantly less than liver, which appears to be the non-haematopoietic organ that demonstrated any significant uptake of the labelled antibody.

The consistency between individual patients and the linear relationship between total activity of $^{90}$Y infused and bone marrow radiation dose may allow simplification of the imaging and dosimetry schedule in the future.

Toxicity:

Infusion of RIC: No adverse effects were seen during the infusion of either $^{111}$In-labelled or $^{90}$Y-labelled anti-CD66 Mab. Side effects typical for TBI associated with non-hematological tissues such as acute nausea, vomiting, fatigue, hair loss and endocrine organ dysfunction are lacking.

Post targeted radioimmunotherapy: No adverse effects or toxicity were seen following infusion of the $^{111}$In-labelled antibody. In all patients, grade 1-4 haematological toxicity was seen, as indicated by a fall in peripheral blood counts, by day 12 after infusion of the $^{90}$Y-labelled antibody. There was a trend for increasing grade of haematological toxicity with total activity of $^{90}$Y infused. One patient experienced transient grade 2 gut toxicity in the form of diarrhea, the remaining 11 patients experienced no other problems from the time of infusion up to the start of the conventional transplant conditioning.

The organ toxicity seen following conventional conditioning therapy and post stem cell transplantation, are summarised in Table 3. As would be predicted for patients receiving conditioning therapy for stem cell transplantation, all patients experienced >grade 3 haematological toxicity. Gastro-intestinal toxicity was comparable to that caused by conventional transplant conditioning, particularly that caused by high dose melphalan. One patient (patient 5) developed asymptomatic atrial fibrillation on the fourth day following stem cell infusion, serum potassium at the time was low. They were subsequently found to have biochemical evidence of hyperthyroidism with an elevated T4 and low TSH. The patient received beta-blockade and reverted back to sinus rhythm within 48 hours. Thyroid function normalised without further treatment within four weeks. A second patient, who received targeted radiotherapy as part of low intensity conditioning for an allogeneic transplant (fludarabine, melphalan) experienced a rapid rise in bilirubin in the second week following allogeneic transplantation. The bilirubin returned to within the normal range after withdrawal of norethisterone and itraconazole.

Engraftment

The time to recovery of peripheral blood total white cell, neutrophil and platelet counts are summarised in Table 4. In 18/20 patients full engraftment was achieved and within predicted time periods. In one patient (patient 7) a sub-optimal CD34 positive cell dose was given resulting in delayed neutrophil and platelet engraftment. This patient had relapsed following an earlier autologous stem cell transplant for myeloma and received a second transplant with targeted radiotherapy in addition to high dose melphalan. A second patient had partial engraftment by day 100 becoming transfusion independent by day 20. In this patient it had been difficult to mobilise peripheral blood stem cells and the transfusion of autologous cells had required 2 days to complete. This will have contributed to the delay in cell count recovery. 19/19 patients have had bone marrow aspirates performed at day 100 post transplantation, all but 1 were normocellular.

No late graft failures have been seen in this patient group with follow up between 3-24 months. Chimerism analysis for patients that received allogeneic transplants (patients 8, 9, 13 and 14) showed full donor engraftment by day 30 post transplant, all have remained fully donor and are in complete remission (follow up 18-24 months).

Clinical Responses

Although the main goal of this study is to evaluate pharmacokinetic, biodistribution and toxicity of radiolabelled anti-CD66 MAb, clinical responses will be followed up in addition.

The first patient (001) for this study starting with radiation level 1 received RIC as part of transplant conditioning in March 2001—the last patient (020) at radiation level 4 was treated in October 2005. The intended follow up time is up to 1 year for toxicity assessment and 3 years for disease response.

First results indicate the expected highly efficacious treatment of RIC with respect to progression free survival and overall survival. Interim results of a follow up in May 2005 are presented in Table 5. Results suggest that radiation doses higher than 25 MBq/kg bodyweight may induce a high rate of complete remissions in multiple myeloma patients.

However, clinical efficacy with respect to progression free survival and overall survival in haematological diseases will be the focus of subsequent clinical trials.

Conclusions:
1) No toxicity was associated with infusion of either $^{111}$In-labelled or $^{90}$Y-labelled anti-CD66 Mab.
2) No increase in post transplant toxicity over those expected following conditioning for stem cell transplantation. One patient experienced transient rise in thyroid activity with associated atrial fibrillation. The patient subsequently became hypothyroid.
3) All patients engrafted, 13 of 14 with average time to engraftment the same as for patients undergoing conventional stem cell transplants. Two patients had delayed recovery of neutrophils and platelets, possibly related to low CD34 cell dose available for transplant. There have been no late toxicity or delayed marrow failures with a follow-up of 3-36 months (mean 18 months).
4) Excellent bone marrow targeting was seen in 20 of 21 patients. One patient had significant liver uptake and low marrow targeting, but still higher than the liver and received therapy. On review the bone marrow in this patient had only 5-10% cellularity indicating the probable cause for the lower BM to liver ratio. The second patient had borderline dosimetry and did not receive targeted radiotherapy but went onto a conventional transplant.
5) Organ dosimetry showed a highly favourable dose distribution with the bone marrow receiving between 4-10 fold higher estimated radiation dose than the liver. These results obtained with the anti-CD66 MAb compare favourably with other published targeted radiotherapy vectors such as anti-CD33 or anti-CD45.
6) The maximum tolerated radiation dose delivered by the anti-CD66 MAb has not been reached.

Discussion:

Results of the Dose Escalation Study

The results of the study summarised above indicate that the anti-CD66 MAb is well tolerated and has the ability to deliver 4-10 fold excess radiation dose to the bone marrow compared with the liver. Significant radiation was also delivered to the spleen. No additional significant toxicity was seen in the patients treated to date. Peripheral blood leucocyte and platelet counts fell significantly after the therapeutic dose of targeted radiation, particularly in the highest dose level, indicating a definite myelosuppressive effect. The majority of patients that have received the highest radiation dose to date experienced longer total periods of neutropenia during their transplant, as they were already neutropenic before receiving high dose therapy. This may require the earlier use of prophylactic antimicrobials. The use of targeted radiotherapy did not appear to adversely affect the subsequent engraftment of stem cells, either autologous or of donor origin. No late marrow failures have been seen.

In the two patients that have received sibling stem cell transplants for poor risk AML using targeted radiotherapy as part of low intensity conditioning schedule, full donor chimerism was achieved at day 30 post transplant. Similarly, the two patients that have undergone allogeneic (sibling) transplants for multiple myeloma are in complete remission from the disease 2 years after receiving RIC as part of their transplant conditioning.

The MTD of radiation has not yet been reached. However, in the final dose level (37.5 MBq/kg) maximum radiation dose limits of 12 Gray to the liver and 35 Gray to the bone marrow were set. Estimated absorbed radiation doses delivered to the marrow at the fourth dose level, 17-30 Gy, are already in excess of that provided by external beam radiotherapy (TBI).

Selection of CD66 as the Target Antigen

CD66 is a member of the myeloid cells family of membrane and protoplasm proteins, with only CD66e being a member of the carcinoembryonic antigen (CEA) family of membrane proteins which is itself a member of the immunoglobulin super-family of receptors (Beauchemin N. et al., Exp Cell Res., 1999, 252: 243-249). The antigen 'CD66' actually consists of several structurally related glycoproteins, CD66a-f, four of which (CD66a-d) are expressed by neutrophils. CD66 cluster members also have other designations—CD66a is also termed biliary glycoprotein (BGP) or cell adhesion molecule-1 (CEACAM-1); CD66b as CGM6, non-specific cross-reacting antigen 95 (NCA95) or CEACAM-8; CD66c as NCA50/90 or CEACAM-6; CD66d as CGM1 or CEACAM-3. Regarding the CEA-cluster members not present on haematopoietic tissue, CD66e or CEA and CD66f as the pregnancy specific glycoprotein.

Structurally the CD66 cluster members contain an amino-terminal domain of 108-110 amino-acids homologous to the immunoglobulin variable domain, followed by a variable (0-6) number of Ig C2-related domains.

CD66 family members are thought to function as cell adhesion molecules interacting with E-selectin, galectins and type 1 fimbriae of *Escherichia coli* (Skubitz K. M. et al., J Biol Regul Homeost Agents, 1999, 13: 240-251).

The CD66 antigens a-d are expressed on normal myeloid cells from the promyelocyte stage through to mature neutrophils. They are also up-regulated by neutrophil activation signals. Expression on acute myelogenous leukemic blasts is poor with only 6.8% of AML blasts expressing any CD66 antigens. However, 66.7% of B-lineage ALL blasts aberrantly expressed CD66 antigens (Carrasco M. et al, Ann Hematol, 2000, 79: 299-303). FACS analysis of bone marrow samples from patients with multiple myeloma demonstrate expression of CD66 by plasma cells in the majority of patients. In addition, one patient in the phase I study showed focal uptake of $^{111}$In-labelled antibody at a site of a lytic lesion (images in enclosed study report).

Thus, as a potential vector for targeted radioimmunotherapy for multiple myeloma, MAb BW 250/183 will be effective to induce not only remission in bone marrow but may also target focal disease, including extramedullary sites. The ability for the anti-CD66 MAb to bind to plasma cells in vitro and in vivo will be further assessed in a phase II study.

The results from the dose escalation phase I study have shown that significant doses of radiation can be delivered to the bone marrow and spleen by the anti-CD66 MAb (BW 250/183), two to five times that of the nearest non-haematopoietic organ (liver). In addition, no significant uptake was seen by other tissues expressing CEA antigens (gut, epithelium). These results are consistent with those published by the Ulm group using a similar anti-CD66 MAb with one significant difference: in the Ulm series renal uptake of radiation was high with 17% of patients developing delayed renal toxicity. This was due to the use of the strongly reduced molecule of anti-CD66 Mab and due to the selection of highly electronegative rhenium-188 ($^{188}$Re) as the therapeutic radionuclide (Bunjes D. et al., Blood, 2001, 98: 565-572). The most likely explanation for the renal toxicity is that the $^{188}$Re immunoconjugate was unstable in vivo, free $^{188}$Re accumulated in the renal parenchema resulting in higher radiation doses to these organs. In our experience using $^{90}$Y-labelled anti-CD66 there is no significant renal uptake of radiation and no patients have developed renal impairment.

Furthermore, the personalized treatment procedure consisting of a subsequent use of $^{111}$In-labelled anti-CD66 MAb for imaging and exact calculation of $^{90}$Y dosimetry adjusted to lean body weight followed by $^{90}$Y-labelled anti-CD66 MAb for bone marrow conditioning allows an optimized treatment of each individual patient guaranteeing high efficacy at no additional toxicity.

The invention claimed is:

1. A method for treating multiple myeloma, the method comprising a therapeutic step of administering a therapeutic radioimmunoconjugate (RIC) to a human subject suffering from multiple myeloma, wherein the therapeutic RIC comprises a CD66-binding component and radionuclide yttrium-90 ($^{90}$Y), the CD66-binding component being (1) a BW250/183 antibody in the murine, humanized, or recombinant form and (2) covalently linked to the radionuclide via chelating agent isothiocyanato-benzyl-S-methyl-diethylenetriaminepentaacetic acid (ITC-2B3M-DTPA).

2. The method of claim 1, further comprising, prior to the therapeutic step, an imaging step of administering to the subject an imaging RIC that comprises a CD66-binding component and an imaging radionuclide, the CD66-binding component of the imaging RIC being a BW250/183 antibody in the murine, humanized, or recombinant form.

3. The method of claim 2, wherein the imaging radionuclide is indium-111 ($^{111}$In).

4. The method of claim 2, wherein the CD66-binding component of the imaging RIC and the CD66-binding component of the therapeutic RIC are identical.

5. The method of claim 1, wherein the CD66-binding component of the therapeutic RIC is a BW 250/183 antibody in the murine form.

6. The method of claim 4, wherein the CD66-binding component is a BW 250/183 antibody in the murine form.

7. The method of claim 1, wherein the RIC is administered in a dose of ≥ about 10 MBq/kg body weight (bw), ≥ about 15 MBq/kg bw, ≥ about 20 MBq/kg bw, ≥ about 25 MBq/kg bw, ≥ about 30 MBq/kg bw, or ≥ about 35 MBq/kg bw.

8. The method of claim 1, wherein the method further comprises administering an antitumor agent, an immunosuppressive agent and/or stem cell transplantation.

9. The method of claim 8, wherein the antitumor agent is high dose melphalan (HDM), low dose melphalan (LDM), or a combination of high dose melphalan (HDM) or low dose melphalan (LDM) with other suitable antitumor agents.

10. The method of claim 2, wherein the method comprises the steps:
(a) administering an imaging RIC to the subject;
(b) administering a therapeutic RIC to the subject;
(c) administering at least one antitumor agent and/or an immunosuppressive agent to the subject; and
(d) transplanting autologous or allogeneic stem cells.

11. The method of claim 1, wherein the method further comprises administering an antitumor agent, administering an immunosuppressive agent, or stem cell transplantation.

* * * * *